(12) United States Patent
Hansen et al.

(10) Patent No.: US 7,172,623 B2
(45) Date of Patent: Feb. 6, 2007

(54) CANNULA STENT

(75) Inventors: Palle M. Hansen, Bjaeverskov (DK); Fred T. Parker, Unionville, IN (US); Michael Ehrlinspiel, Württemberg (DE)

(73) Assignees: William Cook Europe ApS, Bjaeverskov (DK); Cook Incorporated, Bloomington, IN (US)

( * ) Notice: Subject to any disclaimer, the term of this patent is extended or adjusted under 35 U.S.C. 154(b) by 631 days.

(21) Appl. No.: 10/267,385

(22) Filed: Oct. 9, 2002

(65) Prior Publication Data

US 2003/0088310 A1 May 8, 2003

Related U.S. Application Data

(60) Provisional application No. 60/335,209, filed on Oct. 24, 2001, provisional application No. 60/342,864, filed on Oct. 22, 2001, provisional application No. 60/346,988, filed on Oct. 19, 2001, provisional application No. 60/327,862, filed on Oct. 9, 2001.

(51) Int. Cl.
*A61F 2/06* (2006.01)
(52) U.S. Cl. .................................... 623/1.15
(58) Field of Classification Search .............. 623/1.15, 623/1.16, 1.11, 1.12, 1.2; 606/191–198
See application file for complete search history.

(56) References Cited

U.S. PATENT DOCUMENTS

| 4,445,896 A | 5/1984 | Gianturco |
|---|---|---|
| 4,494,531 A | 1/1985 | Gianturco |
| 4,503,569 A | 3/1985 | Dotter |
| 4,580,568 A | 4/1986 | Gianturco |
| 4,687,468 A | 8/1987 | Gianturco |
| 4,733,665 A | 3/1988 | Palmaz |
| 4,800,882 A | 1/1989 | Gianturco |
| 4,907,336 A | 3/1990 | Gianturco |
| 5,041,126 A | 8/1991 | Gianturco |
| 5,102,417 A | 4/1992 | Palmaz |

(Continued)

FOREIGN PATENT DOCUMENTS

GB 1 584 772 * 2/1981

*Primary Examiner*—Kevin T. Truong
(74) *Attorney, Agent, or Firm*—Richard J. Godlewski

(57) ABSTRACT

A stent (30) formed from cannula and having flexible segments (31) and high hoop strength segments (32) alternating therealong. Longitudinal struts or tie bars (41) interconnect the segments. Minimal length reduction of the strut occurs upon expansion. In the high hoop strength segment (32), struts (37) in a zig-zag configuration (Gianturco Z-stent) are initially parallel in the unexpanded strut condition. In the flexible segment (31), struts (58) extend from a respective C-shaped bend (59) to converge at the opposite ends thereof when unexpanded. In one embodiment, certain adjacent struts (39–41) of the hoop segment are spaced apart by elongated openings or gaps (46, 48) interposed therebetween and interconnected at their respective ends (42, 44) to form a T-shaped strut interconnection (45). The selected width (50, 51) of the first and third struts (54, 57) increases toward the ends (47, 48) of the elongated openings (46, 48) adjacent the strut interconnection (45). This strut width increase about one end of the strut significantly reduces the tensile strain exhibited about the opening end when the stent is radially expanded during manufacture. The tip length (52, 55) of the struts about the interconnection (45) is also adjusted (increased) along with the other C-shaped strut interconnections (59, 71) to further distribute the tensile strain developed during radial expansion.

33 Claims, 19 Drawing Sheets

U.S. PATENT DOCUMENTS

| | | |
|---|---|---|
| 5,104,404 A | 4/1992 | Wolff |
| 5,258,000 A | 11/1993 | Gianturco |
| 5,282,824 A | 2/1994 | Gianturco |
| 5,334,210 A | 8/1994 | Gianturco |
| 5,421,955 A | 6/1995 | Lau et al. |
| 5,507,771 A | 4/1996 | Gianturco |
| 5,928,280 A | 7/1999 | Hansen et al. |
| 6,042,606 A * | 3/2000 | Frantzen .................... 623/1.18 |
| 6,190,406 B1 * | 2/2001 | Duerig et al. ................ 623/1.2 |
| 6,231,598 B1 | 5/2001 | Berry et al. |
| 6,309,414 B1 * | 10/2001 | Rolando et al. ........... 623/1.15 |
| 2001/0027339 A1 | 10/2001 | Boatman et al. |

* cited by examiner

CANNULA STENT

CROSS-REFERENCE TO RELATED APPLICATION

This application claims priority of Provisional Applications Ser. No. 60/327,862, filed Oct. 9, 2001; Ser. No. 60/346,988, filed Oct. 19, 2001; Ser. No. 60/342,864, filed Oct. 22, 2001; and Ser. No. 60/335,209, filed Oct. 24, 2001.

This application is related to application Ser. No. 09/464,895 filed Dec. 16, 1999.

TECHNICAL FIELD

This invention relates generally to medical devices and in particular to a stent made from cannula.

BACKGROUND OF THE INVENTION

Stents of both the balloon expandable and the self-expanding type are known that have been cut from metal cannula and expanded for placement, for example, in the vessels of a patient. In a number of designs, the stent can be comprised of first and second segments, one of which exhibits radial strength greater than that of the other. The lesser radial strength segment is then formed to have lateral flexibility greater than that of the first segment at least in the smaller diameter, unexpanded state or condition for delivery through tortuous vessels. This combination of segments provides a stent having both good radial strength as well as lateral flexibility.

One known stent is disclosed in U.S. Pat. No. 6,231,598 B1 issued May 15, 2001, and assigned to one of the assignees hereof. The stent is fabricated from cannula and is defined by one or more longitudinal segments of laterally interconnected closed cells. Each closed cell is defined laterally by a pair of longitudinal struts that are interconnected at each end by a circumferentially adjustable member that deforms to permit circumferential expansion while the length of the cell is maintained by the longitudinal struts. Adjacent ones of the longitudinal segments are joined by flexible interconnection segments that permit the stent to bend laterally, particularly in the unexpanded state, and that are comprised of curvilinear struts that form a series of serpentine bends that distribute lateral bending forces while only allowing a slight overall shortening of the stent. A short strut interconnects a longitudinal segment and an adjacent interconnection segment.

Other cannula stents are known from U.S. Pat. Nos. 5,421,955; 5,102,417; 5,928,280 and 5,195,984. A wire frame stent having a number of stent segments is disclosed in U.S. Pat. No. 5,104,404.

However, a problem associated with certain multiple segment stents is that relatively high tensile strains are produced therein that cause areas of metal fatigue. As a result, after these stents in the expanded state have been subjected to pulsatile expansion and contraction due to blood flow, the high tensile strain areas will eventually fracture. In addition, bending and torsional loads to which the stent is subjected when the patient changes physical position, can also cause metal fatigue and subsequent fracture. By way of example, these multiple segment stents have various peripheral vessel applications such as in the carotid of the patient. In addition, these peripheral stents can be subjected to external forces such as the patient having external pressure applied to a vessel and causing its collapse or deformation.

A further problem associated with certain multiple segment stents is that relatively high tensile strains are produced therein during radial expansion of the stent in manufacture. In particular, nitinol cannula tubes are laser cut to form the basic configuration of the stent in an unexpanded condition. The laser cut cannula stent is then radially expanded to a much larger diameter and then heat set to assume the shape of the larger diameter in a relaxed condition. During the radial expansion of the laser cut stent, significant tensile strain is experienced at various bends or strut interconnections of the stent. Depending on the design of the stent and, in particular, the sharpness of the bend angle, fractures, cracks, or gaps can readily occur in the cannula during the radial expansion of the stent. Significant analysis is typically done on the stent design to address pulsatile metal fatigue during the life of the stent in a patient. However, fractures, cracks, or gaps caused during the radial expansion of the stent in manufacture can result in significantly low manufacturing yields and increased costs of production. Furthermore, high levels of concentrated strain anywhere in the stent can readily lead to subsequent fracture during pulsatile contraction and expansion.

It is also a problem with cut cannula stents that the width of longitudinal portions and, in particular, longitudinal struts have a width that is wider or greater at the outside surface of the cannula tube than the inside passageway or lumen surface of the cannula tube. As a result, the cross-sectional area of the longitudinal strut is asymmetrical and fractures, cracks, and the like more readily form or occur at an inside surface edge of a cut cannula stent.

SUMMARY OF THE INVENTION

The foregoing problems are solved and a technical advance is achieved in an illustrative cannula stent of the present invention wherein at least one longitudinally extending strut that laterally interconnects with other struts at respective ends thereof to form for example a T-shaped or W-shaped strut interconnection is selectively increased in width toward the interconnection to advantageously distribute potential strain experienced thereat during for example radial expansion of the stent and to further advantageously minimize, if not eliminate, fractures, cracks, or gaps at high concentration areas of tensile strain at or near the strut interconnection. Such selective increase in strut width toward a strut interconnection can similarly and advantageously distribute tensile strain during other expansions and contractions of a cannula stent such as with pulsatile expansion and contraction. In particular, the cannula stent includes an elongated member having a passageway extending longitudinally therein and a wall of biocompatible material extending at least partially around the passageway. The wall has a plurality of struts extending longitudinally therein and plurality of elongated openings therethrough and interposed between the struts. First, second, and thirds ones of the struts are adjacent and have respective ends laterally interconnected at a strut interconnection. A first opening extends between the first and second struts and has a first opening end longitudinally adjacent the strut interconnection. A second opening extends between the second and third struts and has a second opening end also longitudinally adjacent the strut interconnection. The first strut has a selected width that increases along the strut toward the first opening end to advantageously distribute tensile strain along the strut and away from the first opening end during at least radial expansion of the stent. Thus, this advantageously lowers high concentration levels of tensile strain about the strut ends and minimizes, if not eliminates, fractures, cracks, or gaps and the like during radial or other expansion and contraction of the stent.

Advantageously, the third strut of the cannula stent also has a selected width that increases along the strut toward the second opening end to likewise distribute tensile strain along the strut during at least radial expansion of the stent. This increase in the selected width of the struts toward the opening ends further advantageously minimizes, if not eliminates, undesirable fractures, cracks, or gaps created during radial or other expansion and contraction of the cannula stent at a high concentration of tensile strain.

The increase of the selected width advantageously increases longitudinally along the strut toward the opening end adjacent the strut interconnection. This further advantageously distributes and lowers tensile strain created during radial and other expansion and contraction of the stent. The increase on either one or both of the first and third longitudinal struts extends at least partially along a length of the strut in a range from 10 to 30 percent of the length of the strut. Preferably, the increase in strut width occurs in a range of 12.5 to 25 percent of the length of the strut and, more preferably, in less then 20 percent of the length of the strut. This advantageously prevents undesirable high concentration of tensile strain from being distributed to or formed at other strut interconnections.

To further distribute tensile strain, the increase in width along a partial length of the strut is equivalent on the first and third struts extending to a strut interconnection.

Another consideration to improve distribution and to lower concentrations of tensile strain particularly during pulsatile expansion and contraction is that the strut interconnection has an appropriate interconnection length that extends longitudinally from the first opening end to the longitudinally opposite edge of the interconnection across from the first opening end. This appropriate interconnection length is greater then the selected width of the strut, preferably the widest selected width of the strut, and is greater then the selected width of the strut in a range of 10 to 30 percent. Preferably, the interconnection length is greater then the selected width of the strut by 15 to 25 percent and, more preferably, when the interconnection length is greater then the selected width of the strut by about 20 percent. Selectively choosing the interconnection lengths of the strut interconnection to be equivalent from the first and second opening ends along with selectively increasing the selected width of the strut further advantageously distributes tensile strain during radial and pulsatile expansion and contraction of the stent.

To further minimize tensile strain and resulting fractures, cracks, or gaps, the elongated openings between adjacent struts are rounded about the opening ends and, more particularly, are at least partially elliptical about the opening ends. The inside diameter width of the strut is more prone to fracturing or cracking than the outside diameter width of the strut and, in particular, about the opening ends. An at least partially elliptical opening end advantageously minimizes or narrows the difference between the inside and outside diameter widths of the strut about the opening end. Thus, the elliptically shaped opening end is advantageously less susceptible to fracturing or cracking than that of a semicircular opening end. In addition, the increase in strut width toward the opening ends can be curvilinear to further minimize fractures, cracks, or gaps. Rounding or smoothing the edges, ends, and sides of the struts and strut interconnections along with the increases in interconnection lengths and selected widths of the struts are combined to more evenly distribute tensile strain along the struts and away from the opening ends.

To yet further minimize tensile strain and resulting fractures, cracks, or gaps, the elongated opening between adjacent struts are rounded about the opening ends and, more particularly, are at least partially elliptical at the opening ends. A cannula stent is advantageously cut with a laser beam directed toward the axis of the cannula tube. As a result, the width of any strut varies from the outside diameter to that of the inside diameter of the cannula tube. A single cut opening is normally uniform in width due to the cylindrical width of the laser beam. However, the width of a multiple laser cut opening, like a strut, can also vary in width from the outside diameter to the inside diameter of the cannula tube. The strut has a outside diameter selected width and an inside diameter selected width that is less than the outside diameter selected width of the strut. In other words, the selected width of the strut along the inside diameter of the cannula tube is less than the selected width along the outside diameter of the cannula tube. As a result, the cross-sectional area of the longitudinal strut is asymmetrical and fractures, cracks, or gaps will more often appear at a strut edge along the inside diameter of the tube during radial or other expansion of the strut during manufacture. To advantageously minimize, if not eliminate, fractures, cracks, or gaps at the inside diameter of a longitudinal strut, the elongated opening adjacent to the strut is formed to have an at least partially elliptical opening thereabout. As a result, the ratio of the inside diameter selected width to that of the outside diameter selected width is increased, and the cross-sectional area of the longitudinal strut becomes more symmetrical. This advantageously minimizes the concentration of tensile strain during expansion and/or contraction of the stent during manufacture and in the patient. This elliptically shaped opening also advantageously decreases the ratio of the inside diameter to the outside diameter selected width of the elongated opening, thus further contributing to the increase in the inside diameter strut width about the elongated end at a strut interconnection and making the cross-sectional area of the longitudinal strut even more symmetrical.

BRIEF DESCRIPTION OF THE DRAWINGS

Embodiments of the present invention will now be described by way of example with reference to the accompanying drawing, in which:

FIG. 16 depicts an enlarged flat view of a T-shaped strut interconnection of the stent of FIGS. 13 and 14 exhibiting tensile strain or stretch therein after radial expansion;

DETAILED DESCRIPTION

Figure 1:
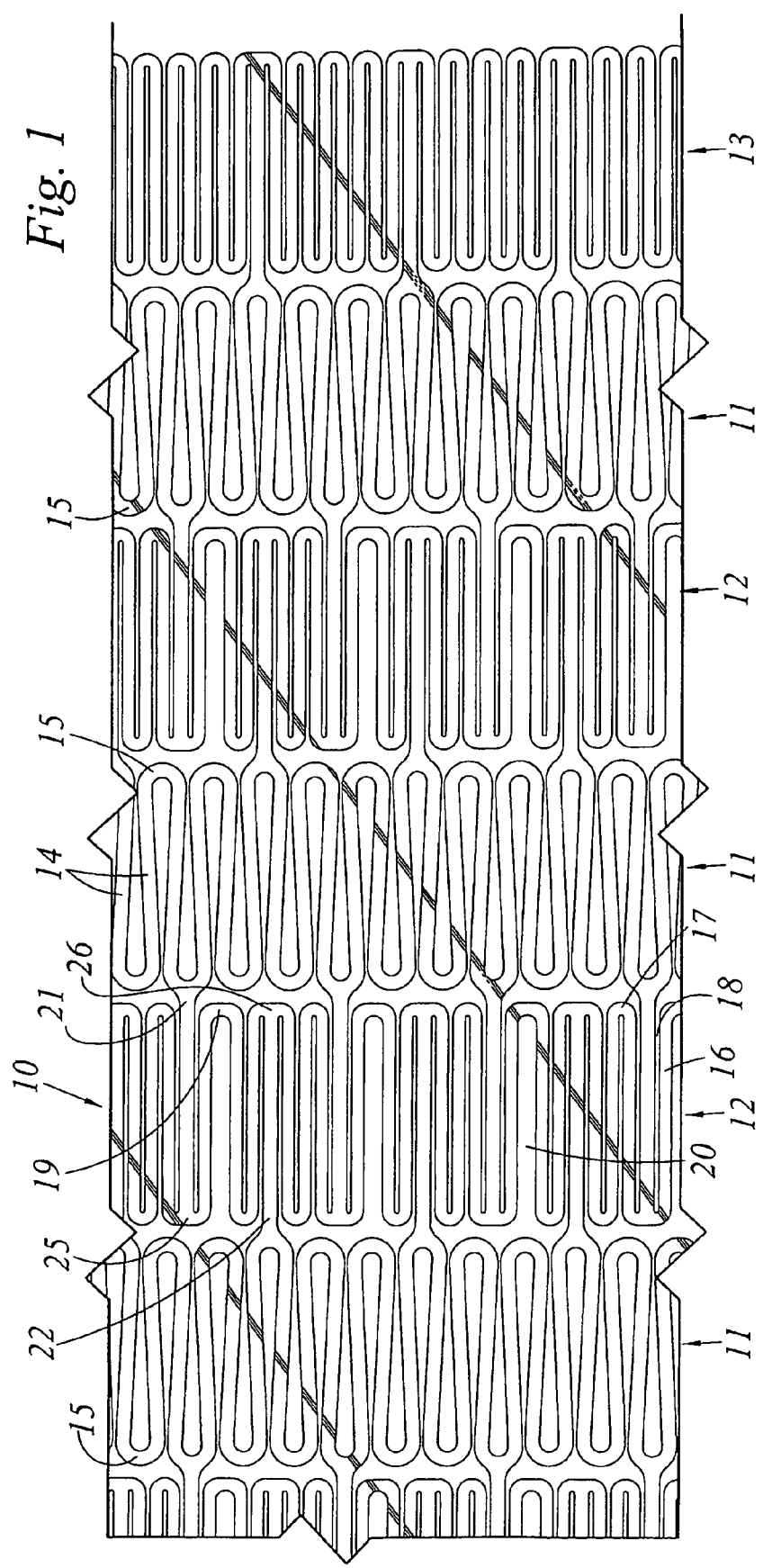
FIG. 1 depicts a flat view of the stent of the present invention cut from a cylindrical piece of cannula.

FIG. 1 depicts a flat view of an illustrative embodiment of stent 10 cut from a cylindrical piece of cannula. The stent includes a plurality of flexible interconnection segments 11 and hoop or higher radial strength cell segments 12, with end cell segment 13 preferably having a high hoop strength. By way of example, the cannula can be comprised of Series 303 or 304 stainless steel that has applications for balloon expandable stents. In another application, the cannula can be formed of a nickel titanium alloy such as nitinol which can be employed for self-expanding stents. These nickel titanium self-expanding stents normally employ the superelastic properties of nitinol. By way of example, the stent is cut from a piece of cannula when in its normal and relaxed condition or state and then is expanded to its larger diameter expanded state. In the larger diameter expanded state, the nitinol material is heat set so that the stent retains its expanded configuration. The stent is then collapsed and introduced into a guiding catheter for deployment at the placement site.

As depicted, the flexible segments 11 are comprised of a serpentine configuration that loops back and forth upon itself with spacing between the struts 14 that varies from one longitudinal end of the segment to the other. Struts 14 project in spaced apart pairs from respective C-shaped bends, interconnections, curves, or bights 15 and then, in the unexpanded stent condition, converge at distal ends that each join to other C-shaped bends, interconnects, curves, or bights 15 to connect with adjacent strut pairs, thus eventually forming a circumferential band.

The hoop cell segments 12 also have a serpentine configuration and are comprised of a series of longitudinal struts 16 that are radially positioned with spacing therebetween that can vary circumferentially. In this embodiment, groups or pairs of adjacent longitudinal struts 16 are laterally or circumferentially interconnected at one end, and each group or pair extends in parallel from a respective C-shaped bend, interconnection, curve, or bight 17 and are closely spaced to define narrow gaps or elongated openings 18, or in parallel from a respective larger C-shaped bend, interconnection, curve, or bight 19 more generously spaced apart to define large gaps 20. The other ends of the struts 16 of each group or pair join to other bends, interconnections, curves, or bights of adjacent strut groups or pairs. Other longitudinal struts or tie bars 21 extend from certain T-shaped or W-shaped bends, interconnections, curves, or bights 25 within large gaps or elongated openings 20 to the right to connect with bends, interconnections, curves, or bights 15 of the adjacent flexible segment 11 disposed to the right leaving narrow gaps between the longitudinal strut or tie bar and the adjacent struts 16 that may be equal in width to narrow gaps 18. Similarly, longitudinal struts or tie bars 22 extend from certain T-shaped or W-shaped bends, interconnections, curves, or bights 26 within large gaps 20 to the left to connect with bends, interconnections, curves, or bights 15 of another adjacent flexible segment 11 disposed on the left of hoop cell segment 12 leavings gaps between the longitudinal strut or tie bar and the adjacent struts 16 that may also be equal in width to narrow gaps 18.

Figure 2:
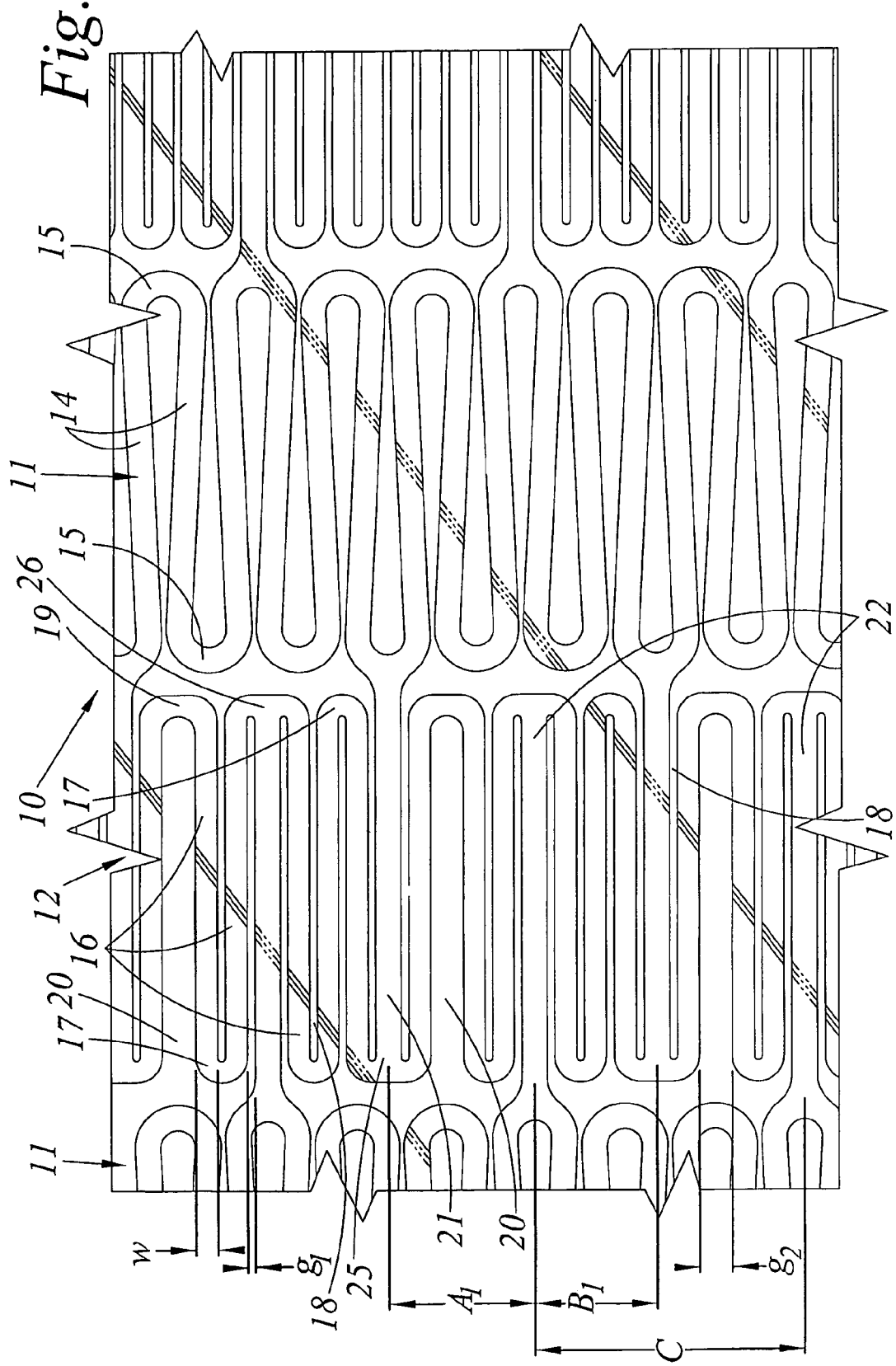
FIG. 2 depicts an enlarged view of the segments of the stent of FIG. 1.
Figure 3:
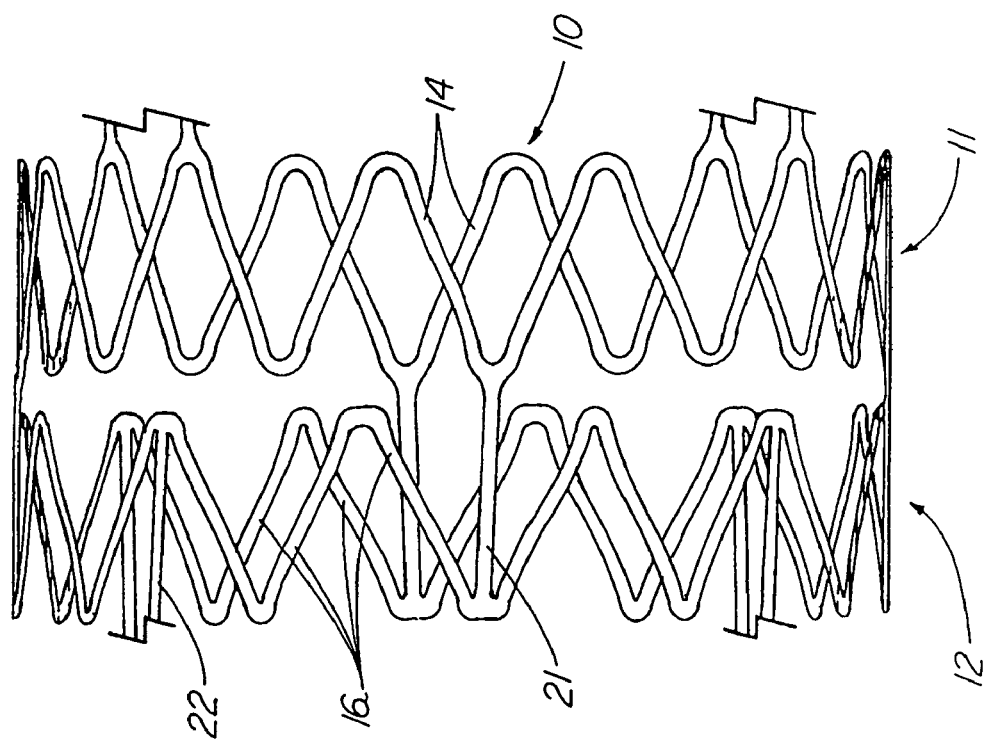
FIG. 3 depicts a side view of the stent of FIG. 1 when in an expanded state.

FIG. 2 depicts an enlarged view of segments 11 and 12 of stent 10 of FIG. 1. In particular and by way of example, longitudinal struts 16 are approximately 0.142 mm in width (w), and narrow gaps 18 therebetween are approximately 0.026 mm wide ($g_1$). Large gap 20 between selected longitudinal struts 16 is approximately 0.194 mm wide ($g_2$). The length and width of the struts can be varied depending on the diameter of the overall stent. By way of further example, the starting cannula diameter of a stent is approximately 1.93 mm and may have a metal wall thickness of 0.215 mm. In this configuration, the hoop cell segments are connected to the flexible segments by longitudinal struts or tie bars 21,22. With a configuration as described and shown, the expanded state of the stent is shown in FIG. 3 with non-uniform spacing, gaps, or openings between the struts of the hoop cell segment.

In FIG. 2, left extending longitudinal struts or tie bars 22 are spaced circumferentially from each other approximately 1.512 mm (C). Right extending longitudinal struts or tie bars 21 interconnecting hoop cell segment 12 with the adjacent flexible interconnection segment 11 extending to the right, are alternated circumferentially with respect to the left extending longitudinal struts or tie bars 22 interconnecting it with the adjacent flexible interconnection segment 11 to the left. However, as shown, the distance $A_1$ between the midlines of longitudinal struts or tie bars 21,22 connecting right adjacent flexible interconnection segment 11 with left adjacent flexible interconnection segment 11 is 0.84 mm. This circumferential distance $A_1$ includes a large gap 20. Midline distance $B_1$ interconnecting adjacent flexible interconnection segments including substantially only narrow gaps 18 of minimal width, is 0.672 mm. As a result, distance $A_1$ is greater than distance $B_1$ with non-uniform spacing between circumferential segments. The total of distance $A_1$ and $B_1$ is approximately 1.512 mm (C).

Figure 4:
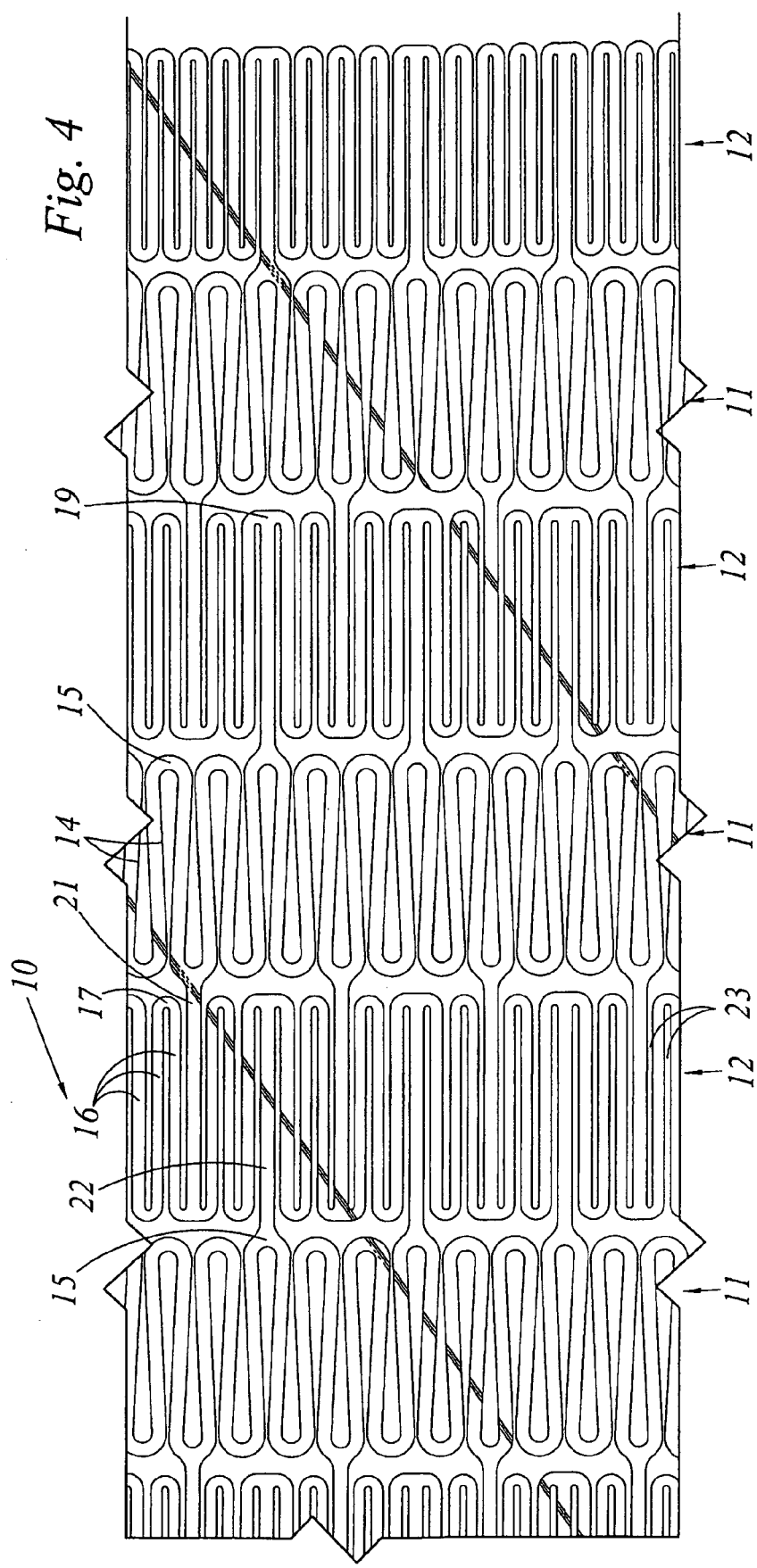
FIG. 4 depicts a flat view of an alternative embodiment of the stent of the present invention cut from a cylindrical piece of cannula.

FIG. 4 depicts a flat view of an alternative embodiment of stent 10 of the present invention cut from a cylindrical piece of cannula. The stent includes a plurality of flexible interconnection segments 11 and hoop or higher radial strength segments 12. As depicted, flexible segments are comprised of a serpentine configuration that loops back and forth upon itself with spacing between the struts 14 that varies from one longitudinal end of the segment to the other. Hoop cell segments 12 are comprised of a series of longitudinal struts 16 that are longitudinally positioned with spacing therebetween that is uniform around the circumference thereof. Best seen in FIG. 5, hoop cell segment 12 has longitudinal struts 16 with medium gaps 23, for example, of 0.047 mm ($g_3$). The width of medium gap 23 is between the widths of narrow gap 18 and large gap 20 of the stent of FIG. 1. As a result, the tensile strains of the stent in FIG. 4 is significantly lower than the tensile strains of the stent in FIG. 1.

Figure 5:
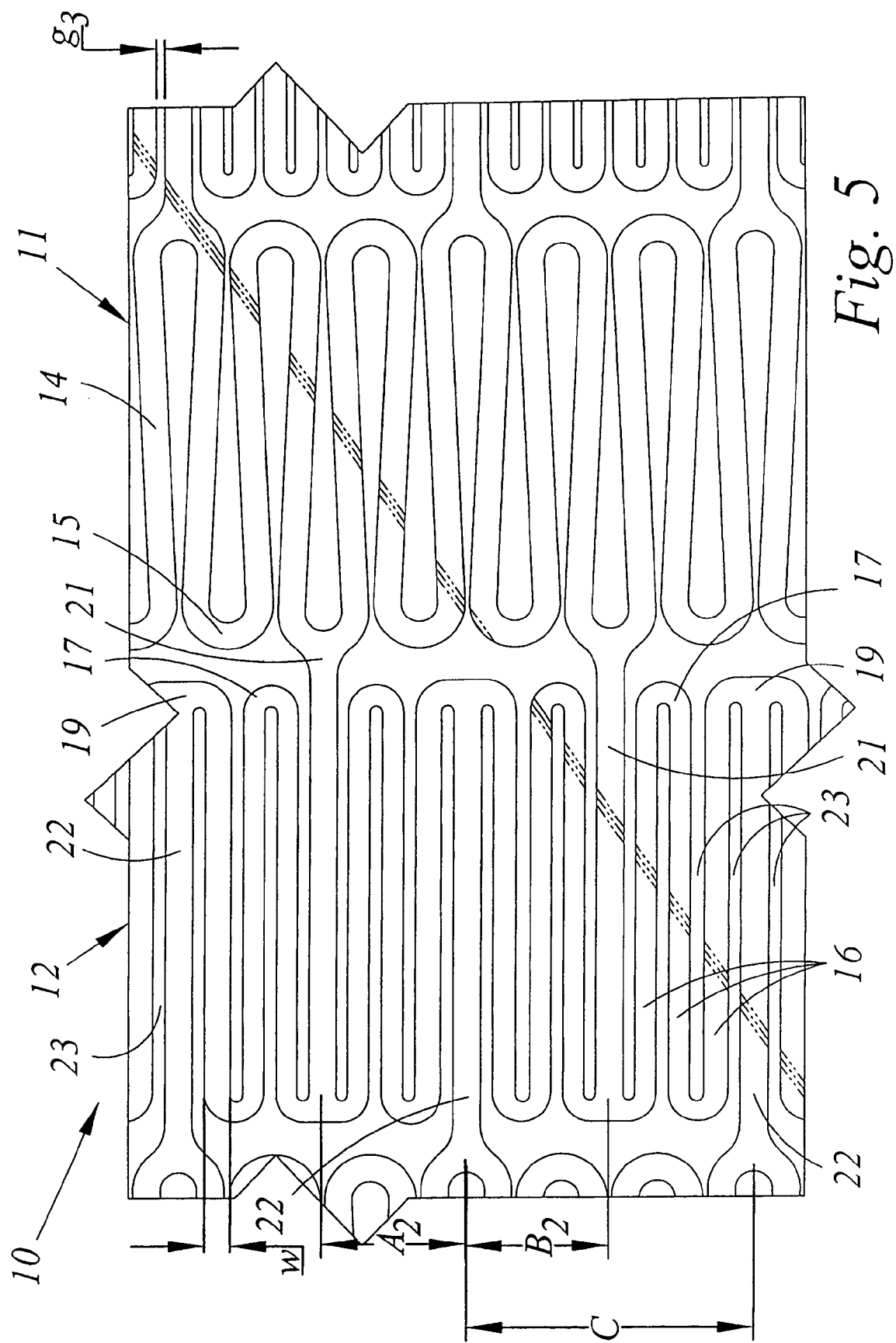
FIG. 5 depicts an enlarged view of the segments of the stent of FIG. 5 with uniformly spaced axial or longitudinal tie bars.

In FIG. 5, uniformly spaced gaps 23 provide for uniform radial expansion of the stent. Longitudinal struts or tie bars 21,22 are spaced circumferentially and uniformly from each other approximately 0.756 mm. The longitudinal struts or tie bars 21,22 interconnecting hoop cell segment 12 with adjacent flexible interconnection segments 11 are alternated circumferentially. However, as shown, the distance $A_2$ between the midline of axial tie bars 21,22 connecting right adjacent flexible interconnection segment 11 with left adjacent flexible interconnection segment 11 is 0.756 mm. This circumferential distance $A_2$ includes medium gaps 23 of approximately 0.047 mm. Midline distance $B_2$ interconnecting adjacent flexible interconnection segments including all uniform medium gaps 23 is again 0.756 mm. As a result, distance $A_2$ and $B_2$ is the same with uniform spacing between circumferential bars. The total of distance $A_2$ and $B_2$ is again approximately 1.512 mm that being the same length as that of C.

Figure 6:
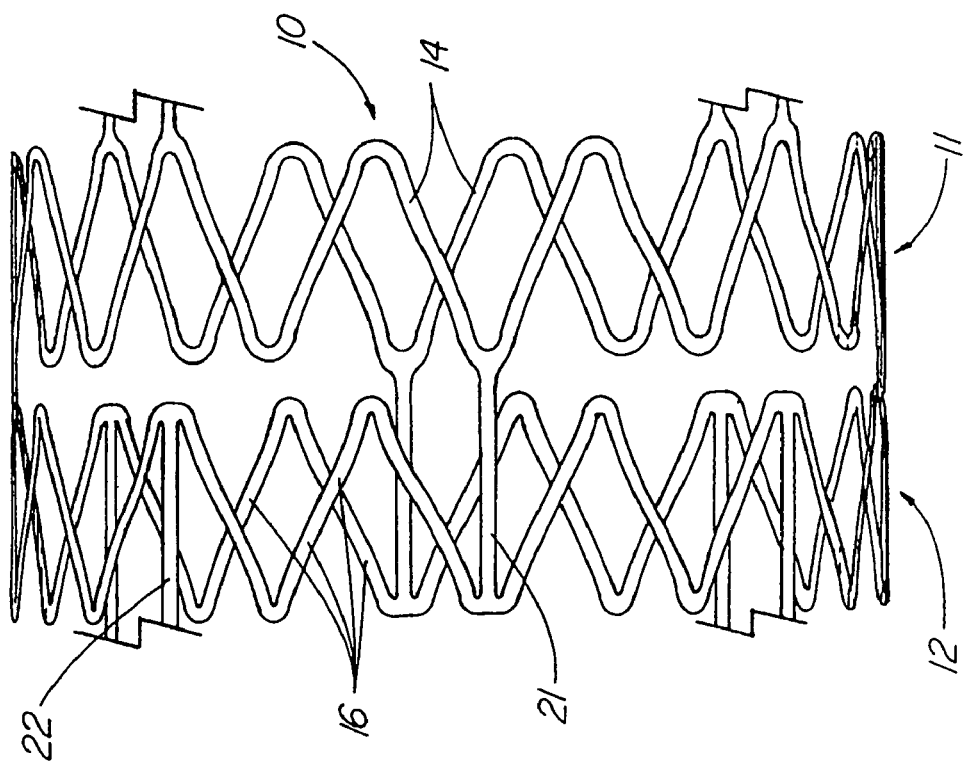
FIG. 6 depicts an expanded side view of the stent of FIG. 5 with the hoop cell segment and the flexible interconnection segment interconnected by longitudinal struts or tie bars.

FIG. 6 depicts an expanded side view of stent 10 of FIGS. 4 and 5 with the hoop cell segment 12 and flexible interconnection segment 11 interconnected by longitudinal struts or tie bars 21,22. The widths of all struts and tie bars in both FIGS. 3 and 6 is sufficiently small, that were the stent to be positioned at a vessel location which is the site of a branch, that flow into or from the branch would not be obstructed to a substantial extent by the stent. In comparison with longitudinal struts or tie bars 21,22 of FIG. 3, the longitudinal struts or tie bars 21,22 of FIG. 6 all remain in a longitudinal orientation. The longitudinal struts or tie bars 21,22 of the stent of FIG. 3 are twisted and are not all longitudinally oriented in the same direction and form various angles of inclination with respect to the longitudinal axis and cause a certain amount of twisting and flexing of the struts during expansion and contraction. This twisting of the longitudinal struts or tie bars provides for excessive fatigue and premature fracture. As previously pointed out, the non-uniform spacing between the longitudinal struts of hoop cell segment 12 of the stent of FIG. 1 causes the twisting of longitudinal struts or tie bars 21,22 and the undesired fatigue therein were the stent of FIG. 1 to be used in an arterial application wherein it would be continuously subjected to pulsatile activity.

Figure 7:
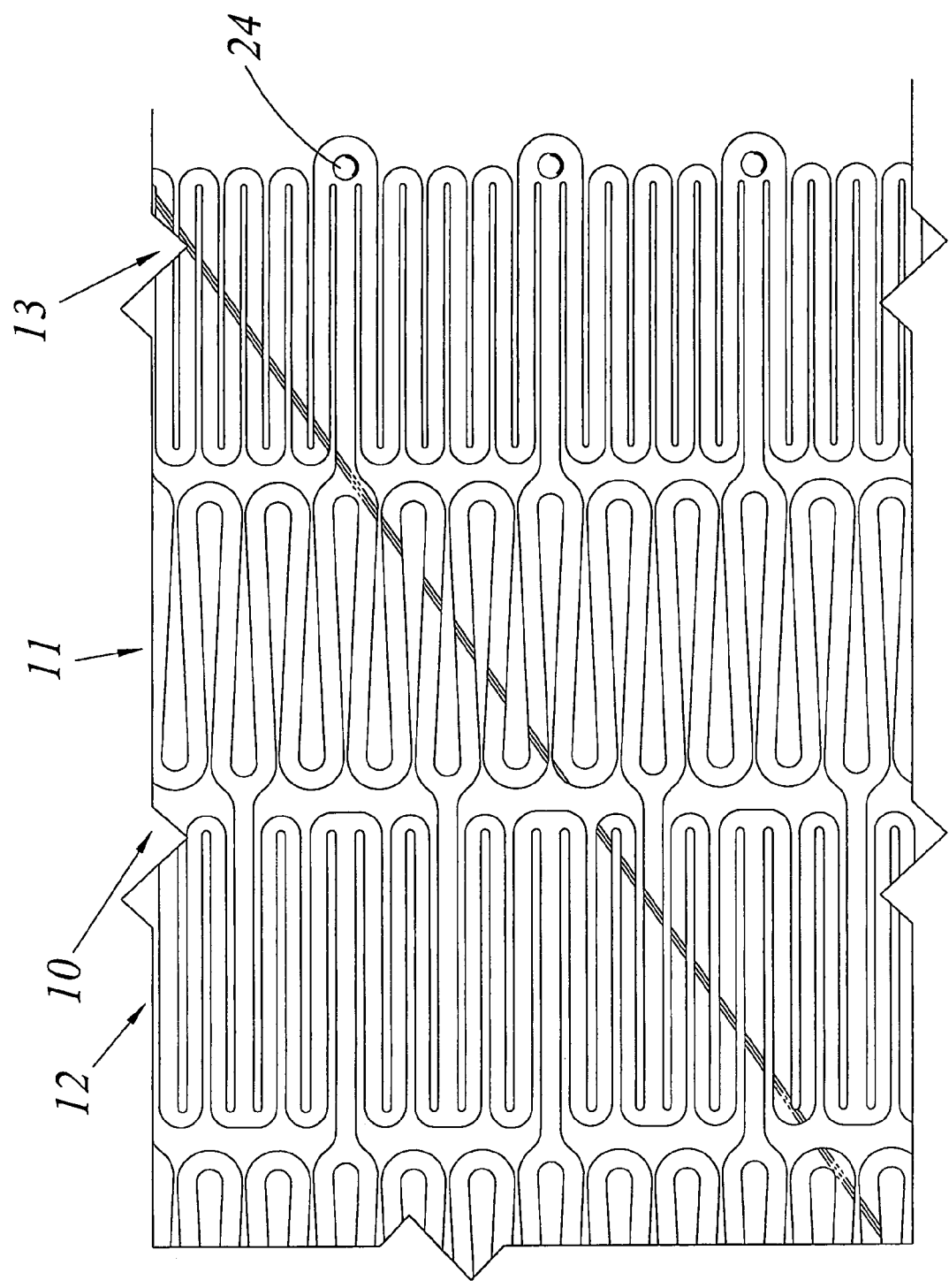
FIG. 7 depicts a flat view of the stent of respective FIGS. 4 and 5 with eyelets at the end cell of the stent.

FIG. 7 depicts an enlarged flat view of a portion of FIGS. 4 and 5 with eyelets 24 at the end cell 13 of stent 10. By way of example, eyelets 24 are approximately 0.23 mm. These eyelets can be filled with various radiopaque materials such as a gold sphere or rivet which are crushed into the aperture.

Figure 8:
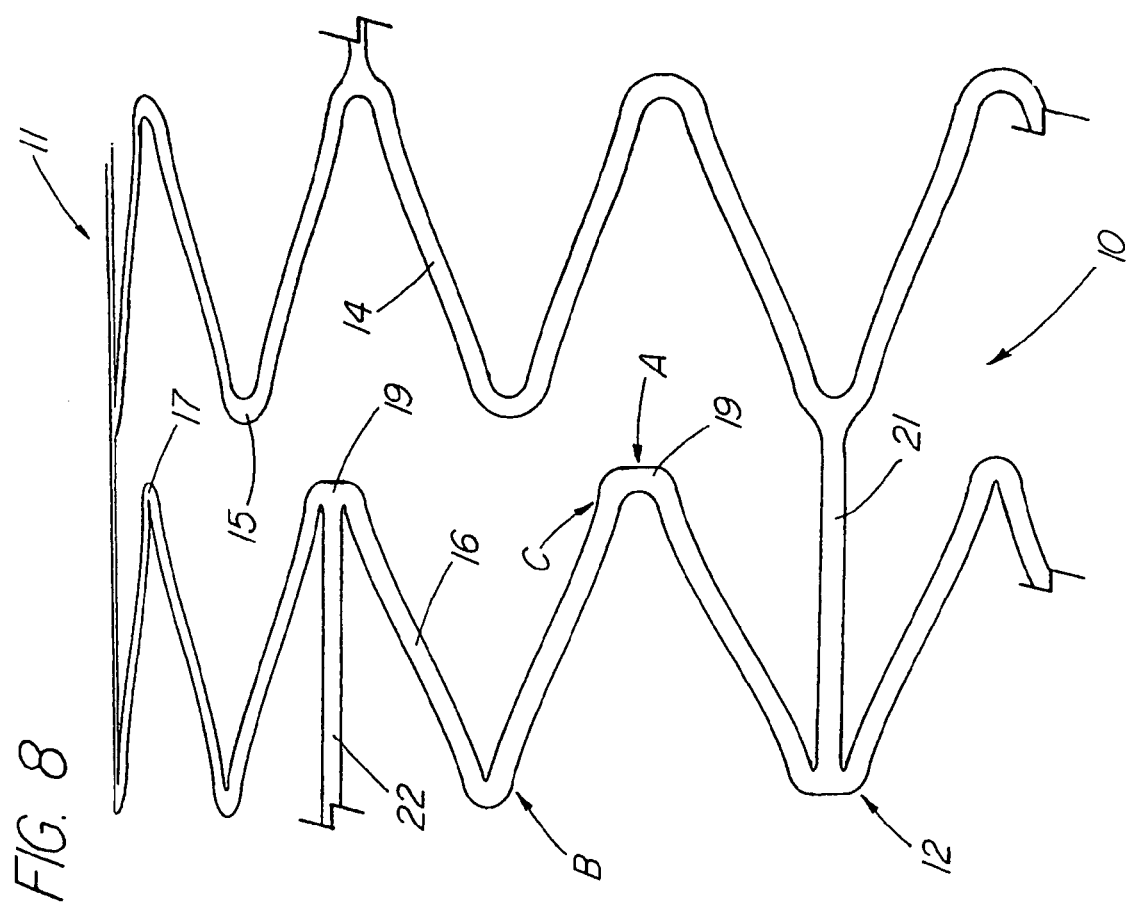
FIGS. 8 and 9 illustrate the stents of FIGS. 1 and 4 respectively in their expanded state.
Figure 9:
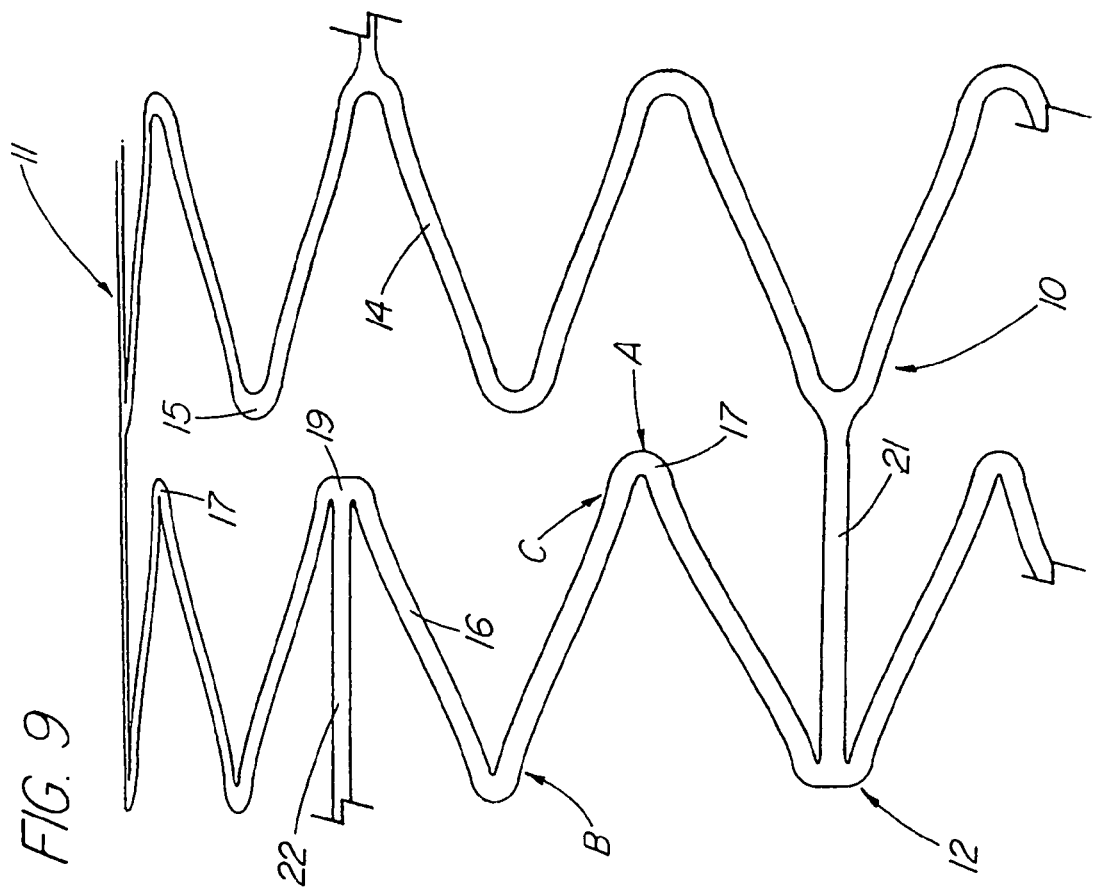

With reference to FIGS. 8 and 9, the stents of FIGS. 1 and 4 have each been expanded to a diameter of about 7.00 mm. Table I below provides a summary of the maximum principle tensile strains, taken at points A, B, and C of high radial strength segment 12, which are the sites of maximum strain.

TABLE I

| STENT DESIGN | STRAIN AT "A" | STRAIN AT "B" | STRAIN AT "C" |
|---|---|---|---|
| FIG. 8 | 0.0119 | 0.0100 | .00816 |
| FIG. 9 | 0.00665 | 0.00772 | 0.00772 |

By way of example, the maximum value for the stent of FIGS. 1 and 8 is about 0.0119 mm/mm while the maximum value for the stent of FIGS. 4 and 9 is about 0.0077 mm/mm, which is approximately 35% lower than that of the tensile strain of the stent of FIG. 1. Thus the stent of FIGS. 4 and 9 is appropriate for applications in vessels having substantial pulsatile events whereby the stent is subject to continuous expansion and contraction cycling.

Figure 10:
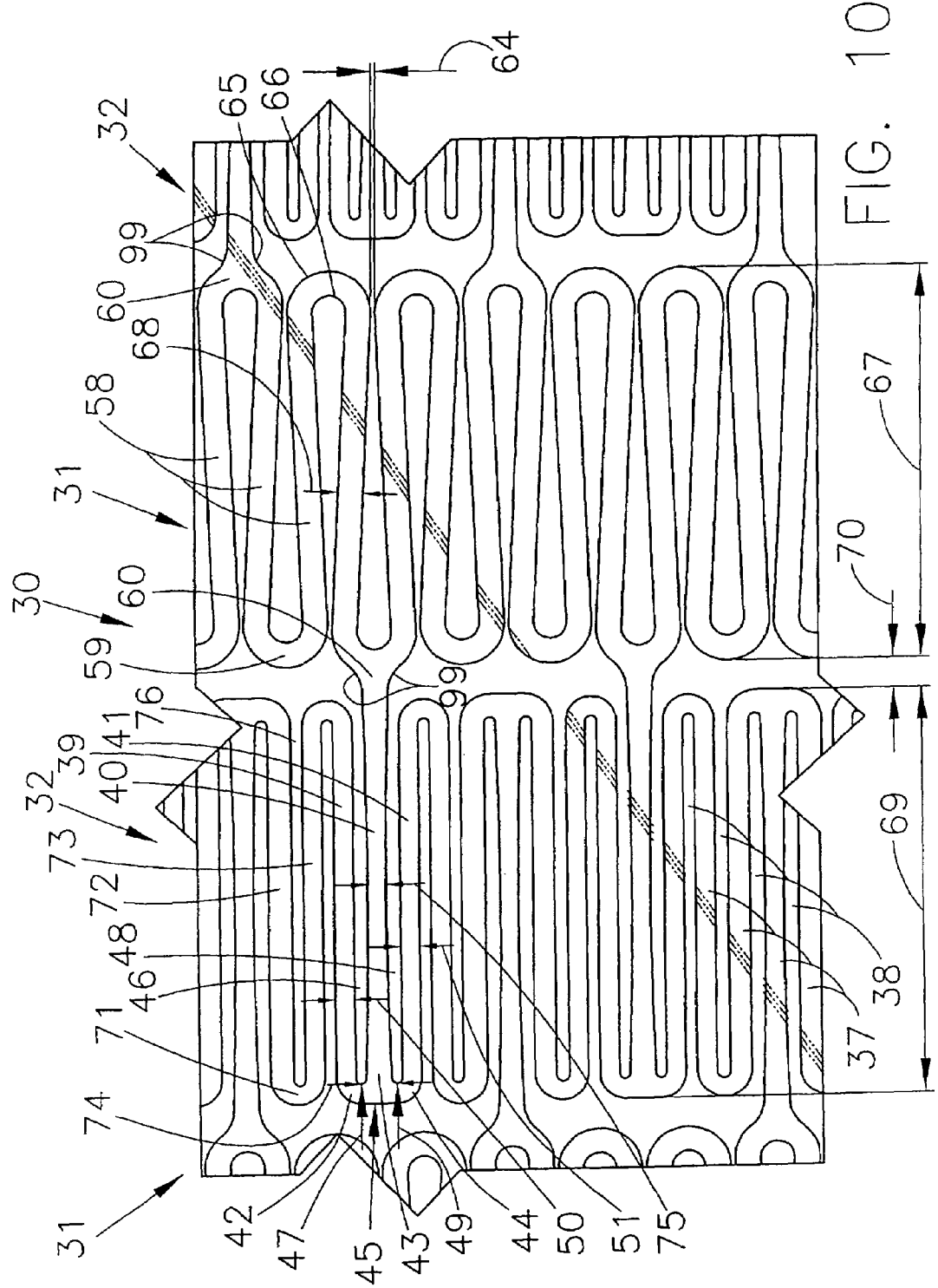
FIG. 10 depicts an enlarged flat view of another illustrative embodiment of the stent of the present invention cut from a piece of cannula.

FIG. 10 depicts an enlarged flat view of another illustrative embodiment of stent 30 of the present invention cut from a cylindrical piece of cannula.

Figure 19:
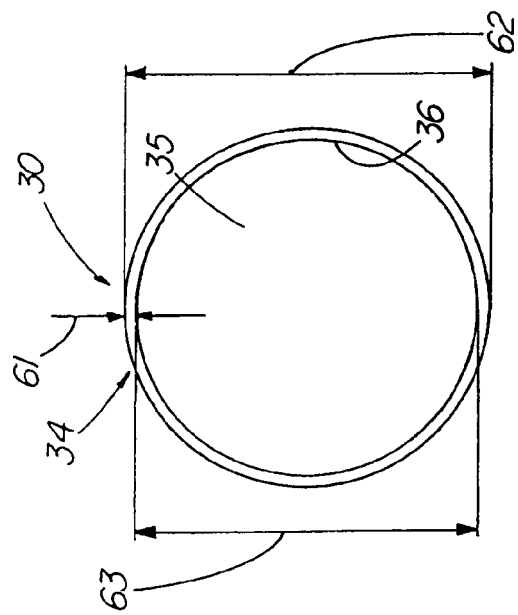
FIG. 19 depicts an end view of the stent of FIG. 10.

FIG. 19 depicts an end view of stent 30 of FIG. 10. Stent 30 comprises elongated member or cannula 34 having a passageway 35 extending longitudinally therein. The elongated member or cannula in an unexpanded condition has an outside diameter 62 of for example 1.9 mm and a nominal inside diameter 63 of for example 1.47 mm with a wall 36 of biocompatible material such as for example stainless steel or nitinol having a nominal thickness of 0.215 mm.

Returning to FIG. 10, stent 30 includes a plurality of flexible interconnection cell segments 31 and hoop or higher radial strength cell segments 32 bounded by end cell segments 33 as previously described (although not shown) and preferably having a high hoop strength. As also previously described, the cannula can be comprised of stainless steel that has applications for balloon expandable stents. In other applications such as being described herein, the cannula can be formed of a nickel titanium alloy such as commercially available nitinol, which can be employed for self-expanding stents. By way of this embodiment, stent 30 is cut from a piece of nitinol cannula when in its nominal diameter or relaxed condition and then is expanded to a larger diameter. In the larger diameter expanded state, the nitinol material is heat set to retain its expanded configuration.

As depicted in FIG. 10, the flexible cell segments 31 are comprised of a serpentine configuration that loops back and forth upon itself with spacing between a plurality of flex cell struts 58 that varies from one longitudinal end of the flex cell segment to the other. Flex cell struts 58 project in spaced apart pairs from respective C-spaced bends, interconnections, curves, or bights 59 and then, in the unexpanded stent condition, converge at the opposite ends. Each opposite strut end then joins to other C-shaped or Y-shaped bends, interconnections, curves, or bights 59 or 60 to connect with adjacent strut pairs, thus eventually forming a circumferential band around the circumference of the stent. By way of example, flex cell struts 58 have a nominal width 68 of for example, 0.141 mm. The minimum longitudinal flex cell gap, opening, or spacing 64 is disposed adjacent C-shaped or Y-shaped bends 59 or 60 and is for example 0.026 mm. C-shaped bend, interconnection, curve, or bight 59 has a outer radius 65 of for example, 0.24 mm, and an inner radius 66 of for example, 0.1 mm. Y-shaped bends, interconnections, bends, curves, or bights 60 are similarly configured and dimensioned except a longitudinal strut or tie bar 40 extends longitudinally therefrom to adjacent hoop cell segment 32. Tie bar end radiuses 99 are for example 0.2 mm.

Hoop cell segments 32 also have a serpentine configuration and, in particular, a well-known zig-zag configuration commonly known as the Gianturco Z-stent configuration. More particularly, hoop cell segments 32 comprise a series or plurality of longitudinal struts 37 having a plurality of elongated openings, spacings, or gaps 38 interposed between the plurality of struts. The longitudinal struts are radially positioned with elongated openings, spacings or gaps therebetween that can vary circumferentially and will be described hereinafter. Certain groups or pairs of adjacent longitudinal struts 72 and 73 extend in parallel from a C-shaped bend, interconnection, curve, or bight 71 and are closely and preferably uniformly spaced to define a narrow space, gap, or elongated opening 76. The other ends of a pair of struts 72 and 73 join with other bends, interconnections, curves or bights of adjacent longitudinal struts. The wall of the nitinol cannula is typically laser cut to form the plurality of struts 37 extending longitudinally therein and the plurality of elongated openings 38 disposed therethrough and interposed between the plurality of longitudinal struts. The plurality of struts 37 includes first, second, and third struts 39, 40, and 41 laterally or circumferentially interconnected at T-shaped strut interconnection 45. The T-shaped strut interconnection could also be considered a W-shaped interconnection; however, the middle longitudinal strut is laterally or circumferentially interconnected with adjacent longitudinal struts at respective ends, thus the T-shaped interconnection designation. First and second elongated openings, spaces, or gaps 46 and 48 terminate at strut interconnection 45 at first opening or gap end 47 and second opening or gap end 49, respectively. First and third struts 39 and 41 have respective selected widths 50 and 51 of approximately 0.141 mm that extend uniformly along the strut. The first and third selected widths 50 and 51 of respective first and third struts 39 and 41 each increases approximately 0.013 mm to 0.154 mm at respective semicircular-shaped first and third opening ends 47 and 49. This increase represents the radius of the approximate 0.026 mm diameter circular laser beam. Second longitudinal strut 40 has a maximum selected width 74 at second strut end 43 of, for example, 0.250 mm, which reduces to a central waist width 75 of for example, 0.160 mm. By way of example, maximum selected width 74 decreases from opening ends 47 and 49 by a 0.013 mm radius arc to a tangent arc having a radius of 10.93 mm. A pair of these tangent arcs form central waist width 74. The 10.93 mm radius tangent arc continues to the other end of strut 40 and makes tangential contact with tie bar end radius 99. As previously suggested, second longitudinal strut or tie bar 40 extends from T-shaped interconnection 45 to a Y-shaped bend 60 of flex cell 31.

By way of further example, hoop cell segment 32 has an overall length 69 of approximately 2 mm. Likewise, flex cell segment 31 has an overall length 67 of approximately 2 mm with spacing 70 between the flex and hoop cell segments of approximately 0.1 mm. The plurality of elongated openings, gaps or spacings 38 between longitudinal struts 37 has a nominal width of, for example, 0.026 mm which is typically uniform along the length of the struts except that the width between first and second struts 39 and 40 and second and third struts 40 and 41 increases due to centralized waist strut width 75, which is positioned approximately at the mid point of second strut 40. Of course, the opening width also varies at the opening end next to the strut interconnection due to the cylindrical laser beam. The indicated strut lengths are for 6 and 7 mm outside diameter stents. Eight, 9 and 10 mm outside diameter stents have strut lengths of for example 2.25 and 2.80 mm, respectively.

Figure 11:
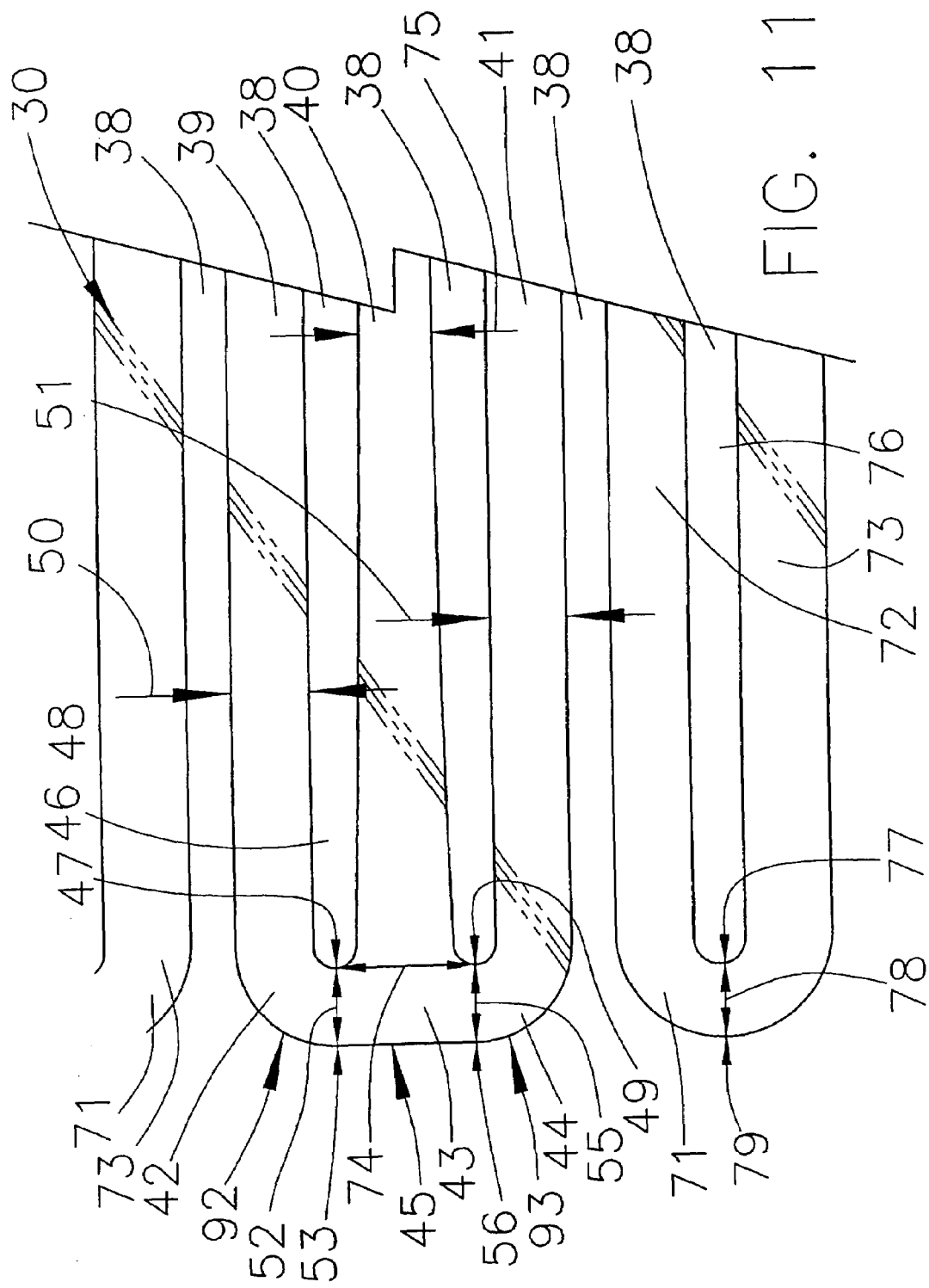
FIG. 11 depicts a further enlarged view of the T-shaped and C-shaped strut interconnections in the hoop cell segment of the stent of FIG. 10.

FIG. 11 depicts a further enlarged view of T-shaped strut interconnection 45 of the stent of FIG. 10 and the struts extending longitudinally therefrom as well as C-shaped bends, interconnections, curves, or bights 71 that are adjacent to the T-shaped strut interconnection on either circumferential side thereof. T-shaped strut interconnection 45 has first, second, and third longitudinal struts 39, 40, and 41 extending longitudinally therefrom as previously described. Likewise, C-shaped bend 71 has first and second struts 72 and 73 extending longitudinally therefrom. T-shaped strut interconnection 45 has a first interconnection length 52 that extends longitudinally from first opening end 47 to first interconnection edge 53. This particular interconnection or strut tip length is for example 0.18 mm. In addition, T-shaped interconnection 45 includes a second interconnection length 55 that extends longitudinally from second opening end 49 to second edge 56 of the strut interconnection. This second interconnection length is for example 0.18 mm and is the same length as first interconnection length 52. Accordingly, this positions first and second opening ends 47 and 49 at approximately the same axial position along the cannula or elongated member, which helps distribute the tensile strain or stretch of the biocompatible material such as nitinol during radial expansion of the cannula. Although the tip lengths could be the same or different, the axial or longitudinal positions of interconnection edges 53 and 56 and opening ends 47 and 49 each could have a different axial or longitudinal position along the length of the stent, elongated member or cannula.

FIG. 11 also depicts C-shaped bends, interconnections, curves or bights 71 which are adjacent to and on either side of T-shaped interconnection 45. C-shaped interconnection 71 has longitudinal struts 72 and 73 extending longitudinally therefrom. First and second C-shaped bend struts 72 and 73 like first and third T-shaped interconnection struts 39 and 41 are approximately 0.141 mm in width with a uniform gap 76 of approximately 0.026 mm. Gap or elongated opening 76 has opening end 77 adjacent to C-shaped bend 71. First and second C-shaped bend struts 72 and 73 have a tip length 78 that extends longitudinally from opening end 77 to first edge 79 of the C-shaped bend. In particular, tip length 78 is for example 0.18 mm and is the same length as first and second T-shaped interconnection lengths 52 and 55. Making these tip lengths approximately the same as well as at the same axial or longitudinal position along the sent helps distribute the strain over the struts during radial expansion of the hoop cell.

Figure 12:
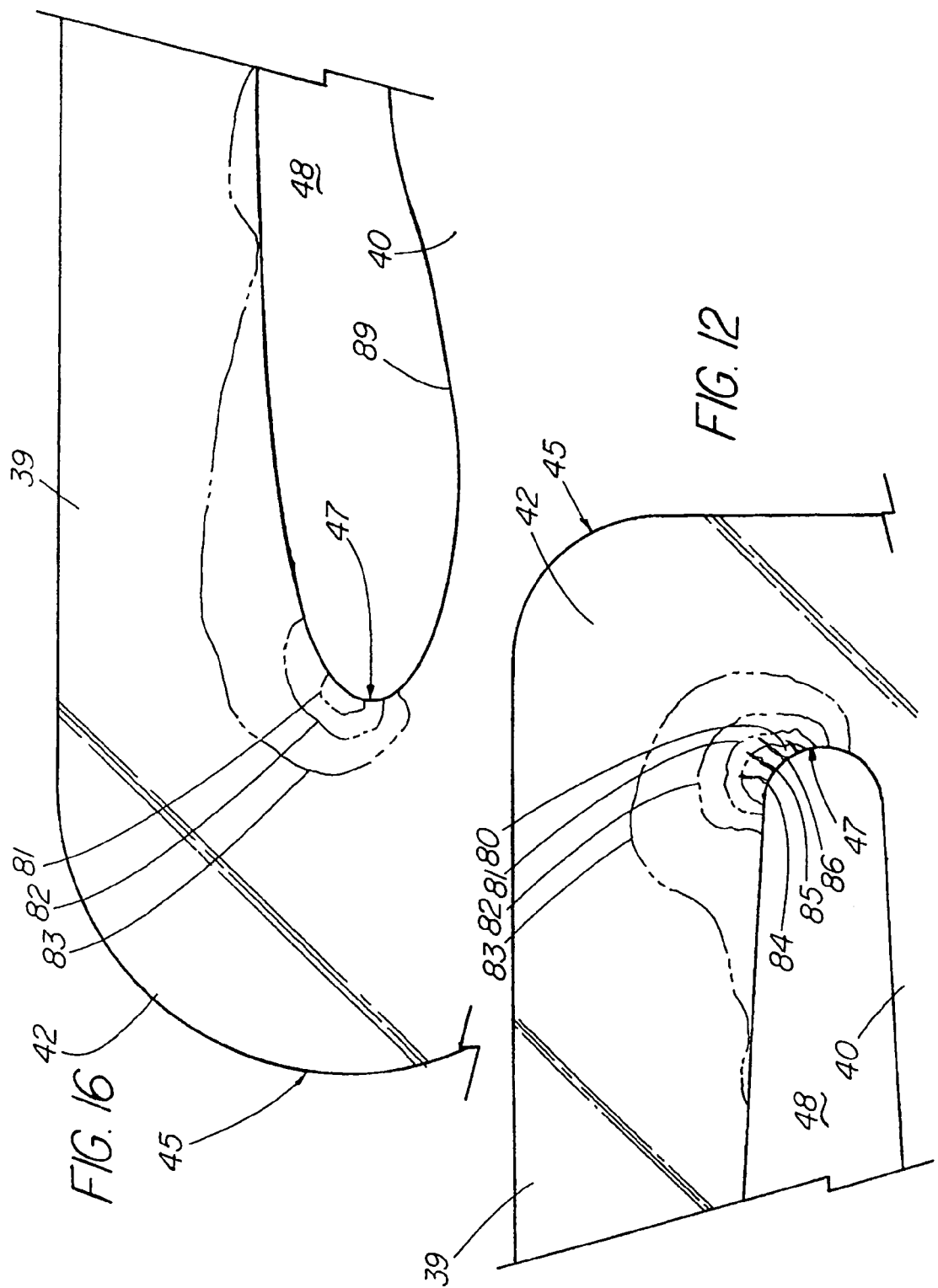
FIG. 12 depicts an enlarged flat view of a portion of a T-shaped strut interconnection of the stent of FIGS. 10 and 11 exhibiting tensile strain or stretch after radial expansion.

FIG. 12 depicts an enlarged flat view of a portion of a T-shaped strut interconnection 45 of the stent of FIGS. 10 and 11 with first strut 39 and second strut 40 exhibiting tensile strain or stretch after radial expansion. After radial expansion, strain is exhibited about first opening end 47 as depicted by strain contour lines 80, 81, 82, and 83. Outside of maximum tensile strain contour line 83, the strain is less then one percent. Between strain contour lines 82 and 83, the strain varies between one and two percent. Between contour lines 81 and 82, the strain varies between two and three percent. Between contour lines 80 and 81, the strain varies between three and four percent. The strain between contour line 80 and first opening end 47 is between four and 5.662 percent. Since there is a high concentration of tensile strain or stretch about first opening end 47 and contour line 80, the result is often that fractures, cracks, or gaps such as fractures, cracks, or gaps 84, 85 and 86 occur in this area and extend into other areas of the strut such as between strain contour lines 80 and 81. These fractures, cracks, or gaps result from the radial expansion of the hoop cell to an enlarged diameter for heat set treatment and more often appear at an edge on the inside surface of the cannula tube. These strain contours were computer generated during a finite element analysis of the stent design and, in particular, the T-shaped interconnection 45 and struts extending therefrom. Since the width of the first and third struts and the first and second tip lengths are approximately the same, similar strain will be experienced at second opening end 49. Not only did a finite element analysis reveal the high concentration of strain at the opening end, but resulting fractures, cracks, or gaps were observed after radial expansion of the hoop cells during manufacture. The occurrence of one or more fractures, cracks, or gaps at the first or second opening ends occurred at a rate between 30 and 40 percent in the expanded stents resulting in an unusually low manufacturing yield rate. Some cracks could be grit blasted or electropolished away during subsequent processing; however, many could not, thus resulting in a low manufacturing yield rate. As a result of this unusually low yield rate, the design of the T-shaped interconnection 45 and the C-shaped bends 71 were evaluated and modified to further distribute the tensile strain throughout the struts and minimize, if not eliminate, resulting fractures, cracks, or gaps.

Figure 13:
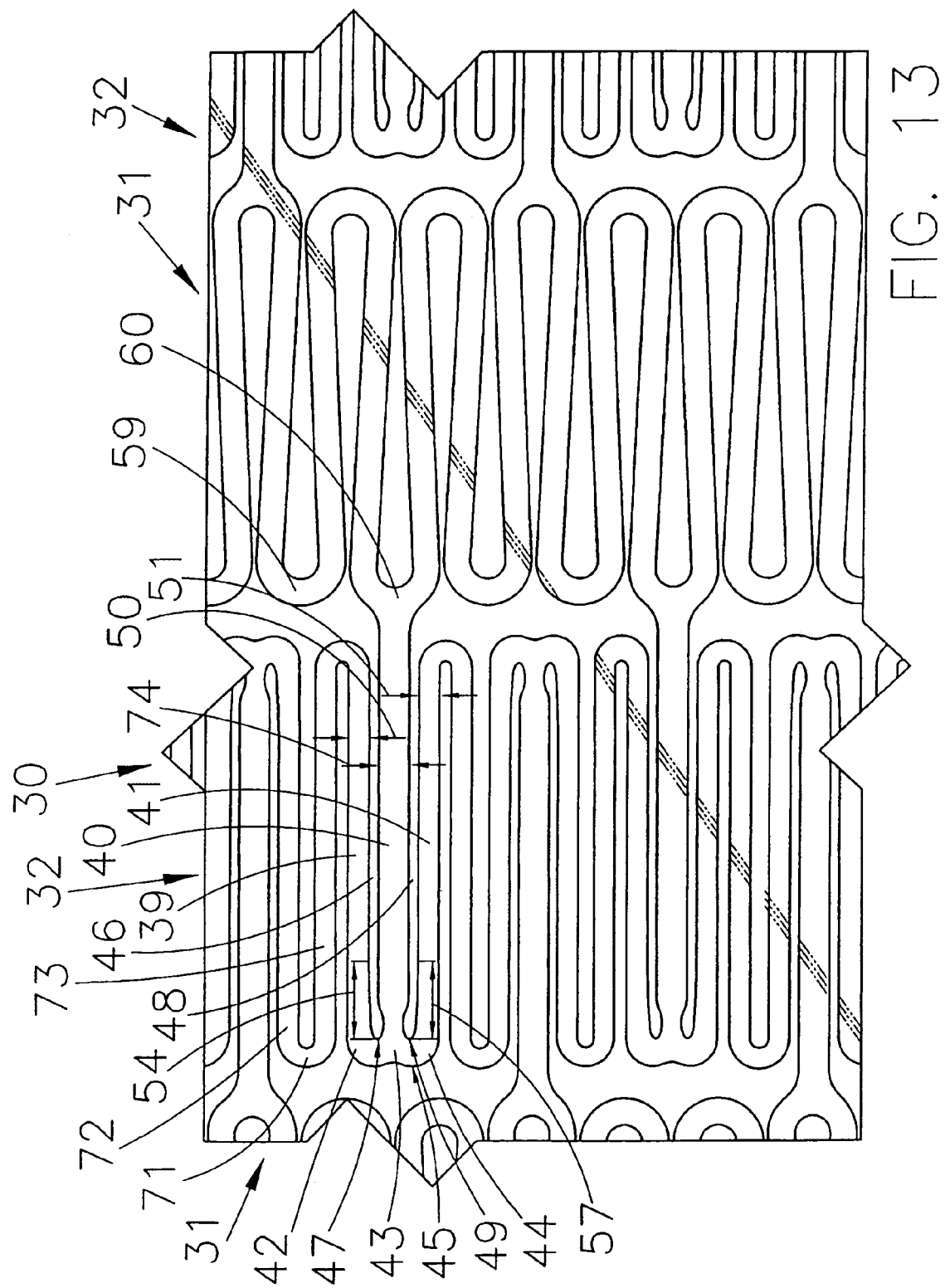
FIG. 13 depicts an enlarged flat view of yet another illustrative embodiment of the stent of the present invention cut from a piece of cannula.

FIG. 13 depicts an enlarged flat view of yet another illustrative embodiment of stent 30 cut from a cylindrical piece of nitinol cannula. This embodiment of stent 30 is similar to the stent of FIG. 10 except that the T-shaped strut interconnection 45; first, second, and third longitudinal struts 39, 40, and 41; and first and second elongated openings 46 and 48 disposed therebetween have been modified from the stent in FIGS. 10, 11, and 12 to better distribute the tensile strain along the struts and away from first and second opening ends 47 and 49. Similarly, the dimensioning of C-shaped bends, interconnections, curves, or bights 59 of flex cell segment 31 have been redesigned to better distribute the strain thereat and to improve the laser cutting of the unexpanded nitinol cannula. Furthermore, C-shaped bends, interconnections, curves, or bights 71 and first and second longitudinal struts 72 and 73 of the hoop cell segment have been redesigned and modified to better distribute strain in the struts thereof.

In particular, second longitudinal strut 40 extending from T-shaped interconnection 45 has a selected maximum strut width 74 of approximately 0.224 mm that extends uniformly for the most part between strut interconnection 45 and Y-shaped bend 60 of adjacent flex cell 31. The narrow waist strut width 75 has been eliminated from this design to help minimize, if not eliminate, the production of slag during laser cutting of the nitinol cannula. As suggested by the finite element analysis of the strain of the T-shaped interconnection, changing the width or the shape of second longitudinal strut or tie bar 40 has very little, if any, effect on the strain experienced at the ends of the first and third longitudinal struts. First, second, and third strut ends 42, 43, and 44 have been modified to more evenly distribute the strain experienced at the ends of first and third struts 42 and 44 during radial expansion of hoop cell segment 32. In particular, the selected nominal widths 50 and 51 of respective first and third struts 39 and 41 increases over at least partial lengths 54 and 57 of respective first and third struts toward opening ends 47 and 49. As a result, the second strut end 43 of second strut 40 has been tapered inwardly on both sides of the strut about second strut end 43. In addition, first and second opening ends 47 and 49 have been enlarged to allow for uniform sand or grit blasting and electropolishing of the stent subsequent to radially expanding and heat setting the stent. The enlarged first and second opening ends 47 and 49 have at least a partial elliptical shape. This at least partial elliptical shape also helps reduce or distribute the tensile strain of first and third struts 39 and 41 as will be subsequently described.

Figure 14:
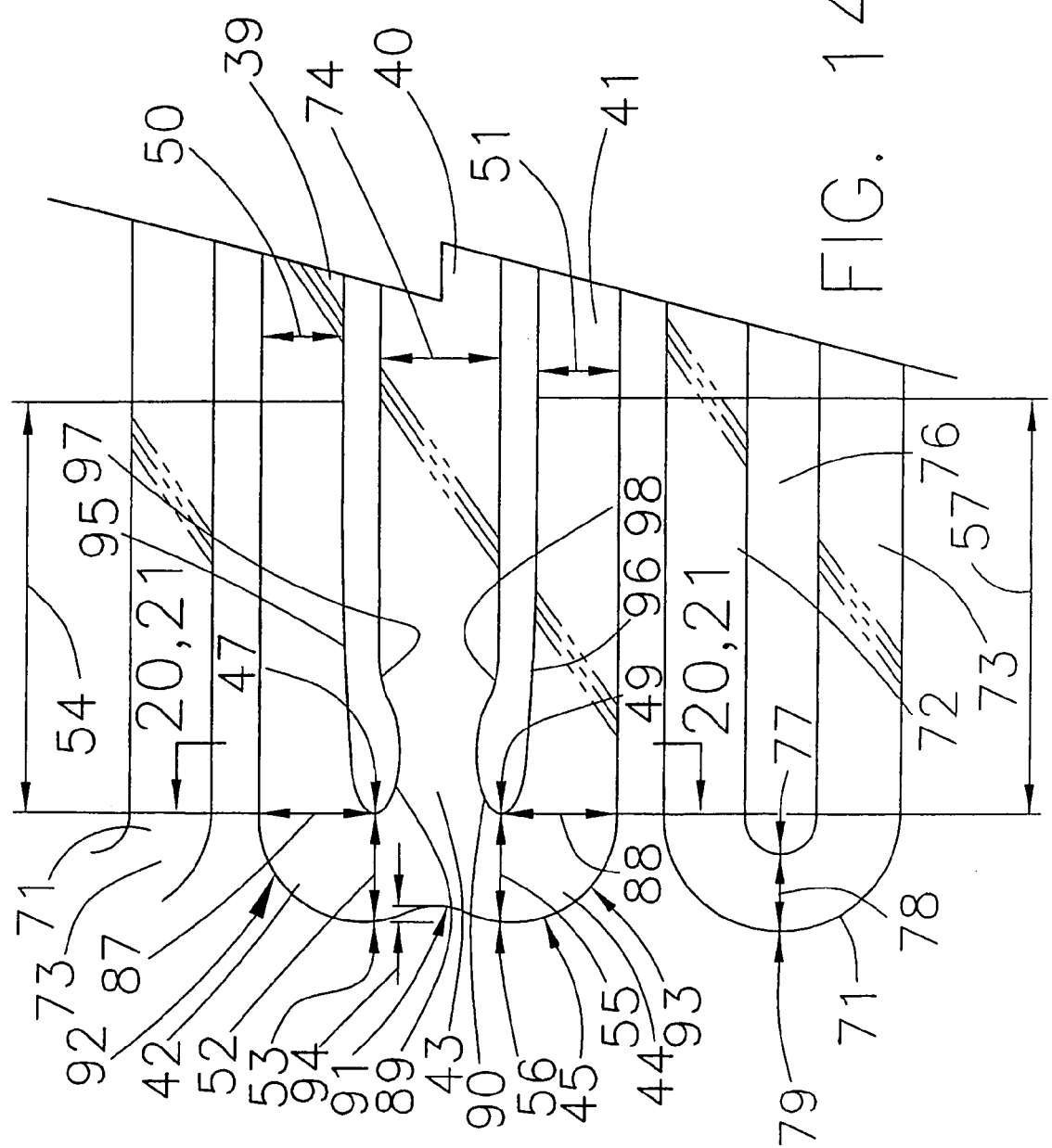
FIG. 14 depicts a further enlarged view of the T-shaped and C-shaped interconnections in the hoop cell segment of the stent of FIG. 13.

FIG. 14 depicts a further enlarged view of T-shaped strut interconnection 45 of the stent of FIG. 13 and the struts extending longitudinally therefrom as well as C-shaped bends, interconnections, curves or bights 71 that are adjacent to the T-shaped strut interconnection on either circumferential side thereof. T-shaped strut interconnection 45 has first, second, and third longitudinal struts 39, 40, and 41 extending longitudinally therefrom as previously described. Similarly, C-shaped bend 71 has first and second strut 72 and 73 extending longitudinally therefrom. T-shaped strut interconnection 45 also has a first interconnection length 52 that extends longitudinally from first opening end 47 to first interconnection edge 53. This particular interconnection strut end tip length has been increased 0.02 mm over that of the stent of FIG. 10 and is for example now 0.2 mm. Similarly, T-shaped interconnection 45 includes a second interconnection 55 that extends longitudinally from second opening end 49 to second edge 56 of the strut interconnection. This second interconnection length has also been increased over the second interconnection length of the stent of FIG. 10 and is for example 0.2 mm and is the same length as first interconnection length 52. This tip length can practically vary from 110 percent to 130 percent of preferably the maximum selected width of the first and third side struts and, in this case, from 0.187 mm to 0.221 mm. More or less than the stated range seriously effects the distribution of stress and strain in the rest of the hoop cell.

Although similarly positioned axially or longitudinally to better distribute strain, tip lengths 52 and 55, edges 53 and 56, and opening ends 47 and 49 can all differ in size and axial or longitudinal position on the stent. Since first and third selected widths 50 and 51 of respective first and third struts 39 and 41 have been increased toward respective opening ends 47 and 49, first and second interconnection lengths 52 and 55 are now circumferentially closer by for example 0.036 mm to a distance of 0.214 mm. To further distribute the tensile strength along first and second struts 39 and 41 and away from opening ends 47 and 49, selected widths 50 and 51 of the respective first and third struts have been increased to first and third selected widths 87 and 88 of for example 0.170 mm. This is an increase of approximately 0.030 mm from the nominal selected width of 0.140 mm of the first and third selected strut widths 50 and 51. A good range of maximum selected strut width can extend from 0.155 to 0.180 mm for a 2 mm long strut having a nominal 0.140 mm selected strut width.

This increase in strut end width increases gradually along at least first and third partial lengths 54 and 57 of the first and third struts toward respective opening ends 47 and 49. By way of example, each of the at least first and third partial lengths is approximately 0.4 mm. A good range for the first and third partial lengths is 0.25 to 0.5 mm for a 2 mm strut length. The at least partial first and second lengths 54 and 57 extend along the increase in strut width for about 20 percent of the 2 mm strut length. These partial lengths can range from 5 to 30 percent, more preferably 12.5 to 25 percent, of the overall length of the first and third struts; but most preferably, the increase in length should extend along 20 percent or less of the length of the first and third struts. This is to lower and better distribute the tensile strain experienced at opening ends 47 and 49 but without distributing unwanted strain to C-shaped bend 71 at the opposite ends of the struts.

First and third opening ends 47 and 49 have been enlarged over that of the corresponding opening end of the stent FIG. 10. This is to allow more uniform sand or grit blasting of the stent during subsequent processing of the stent during manufacture. First and third opening ends 47 and 49 have at least a partial elliptical shape 89 and 90, respectively. The minor and major axes of the at least partial elliptical shapes 89 and 90 are for example 0.04 mm and 0.100 mm, respectively. The center of the elliptical shapes is approximately 0.050 mm from the opening ends. The minor axis is perpendicular to the increasing strut width edge of the strut near the opening end. The increasing selected strut widths increase for example by first and third curvilinear arcs 97 and 98 each having for example a 6 mm radius. The curvilinear arcs and elliptical shapes are tangentially attached. As a result, increasing selected widths 50 and 51 moves each interconnection or tip length circumferentially closer by approximately 0.016 mm. As a further result, first and third increased selected widths 87 and 88 are now for example 0.170 mm. This increase in the selected width helps distribute the strain experienced during expansion of the stent away from the opening end and along the strut. The first and second interconnection tip lengths 52 and 55 are greater than the respective increased selected first and third widths of the first and third struts by approximately 18 percent. However, the interconnection length can be in a range of 10 to 30 percent, more preferably in a range 15 to 25 percent, and most preferably at about 20 percent greater than the selected strut width. This combination of increased tip length as well as increased strut width about the opening ends significantly reduces the tensile strain exhibited in the strut ends about the opening ends during radial expansion of the hoop cell. Furthermore, the increase in the selected width of the first and third struts caused a corresponding decrease in the nominal selected width of second strut or tie bar 40 at the end thereof. Finite element analysis and actual manufacture of the stents indicated no increase in tensile strain of the second strut or tie bar. Advantageously, the fractures, cracks, or gaps previously exhibited at the strut ends about the opening ends were significantly reduced in number if not eliminated. To further distribute the stress and tensile strain about strut interconnection 45, a rounded indentation 91 between first and second edges 53 and 56 was designed therein with a concave radius of for example 0.1 mm extending from the first and second edges into the strut interconnection by a depth 94 of approximately 0.03 mm as depicted.

FIG. 14 also depicts C-shaped bends, interconnections, curves or bights 71 which are adjacent to and on either side of T-shaped interconnection 45. C-shaped interconnection 71 has longitudinal struts 72 and 73 extending longitudinally therefrom. The selected widths of these first and second C-shaped bend struts 72 and 73 have the same selected width as the nominal selected widths of the T-shaped interconnection struts of approximately 0.140 mm with a uniform gap, spacing or opening 76 there between of approximately 0.026 mm. However, in this new design, the tip length 78 of the C-shaped bend 71 has been increased over that of the stent of FIG. 10 to that of for example 0.2 mm, which represents an increase of 0.02 mm. This increase in tip length mimics that of T-shaped interconnection tip lengths 52 and 55 and helps to maintain a better distribution of tensile strain experienced in the strut ends about opening end 77.

Figure 15:
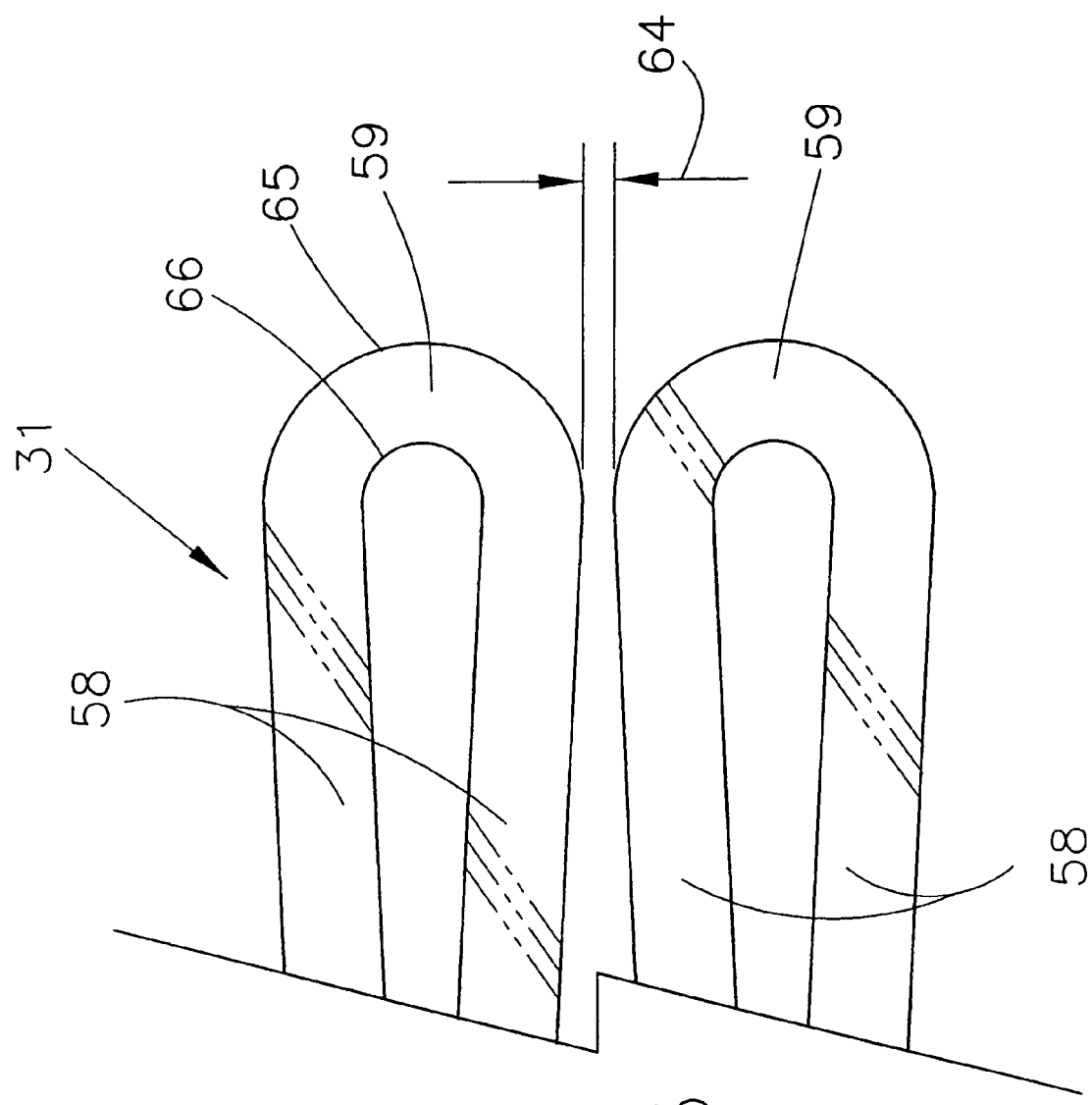
FIG. 15 depicts an enlarged flat view of the C-shaped bends of the flex cell segment of the stent of FIG. 13.

FIG. 15 depicts an enlarged flat view of C-shaped bends, interconnections, curves or bights 59 of stent 30 of FIG. 13 with longitudinal struts 58 extending therefrom in flex cell segment 31. Minimum flex cell strut gap 64 has been increased from that of the stent of FIG. 10 to for example 0.07 mm, which is a significant increase from the 0.026 mm gap of the flex cell struts 58 of the stent of FIG. 10. To facilitate this increase in the gap or opening width, the outer and inner C-shaped bend radiuses 65 and 66 have been changed. The outer C-shaped bend radius 65 has been decreased from 0.24 mm to 0.20 mm. By way of further example, the inner C-shaped bend radius 66 has also been decreased from that of the old 0.10 mm radius to a new radius of for example 0.08 mm. The selected width of the flex cell struts 58 remains the same at for example 0.140 mm. The combination of the strut gap and C-shaped bend radiuses minimized, if not eliminated, the slag during laser cutting of the stent and further distributed the tensile strain in the struts experienced about the C-shaped flex cell strut interconnection.

FIG. 16 depicts an enlarged flat view of T-shaped strut interconnection 45 of the stent of FIGS. 13 and 14 with first and second longitudinal struts 39 and 40 exhibiting tensile strain or stretch after radial expansion. After radial expansion of the hoop cell, strain is exhibited about first opening end 47 with at least partial elliptical shape 89 thereabout as depicted by strain contour lines 81, 82 and 83. Outside of maximum tensile strain contour line 83, the strain is less then one percent. Between strain contour lines 82 and 83 the strain varies between one and two percent. Between contour lines 81 and 82 the strain varies between two and three percent. The strain between contour line 81 and first opening end 47 is between three and four percent. As a result of the increase of the selected width of first strut 39 about first strut end 42 and, more particularly, opening end 47, the strain exhibited in the strut has been reduced from the previously high strain in the range of four to 5.66 percent of the stent of FIGS. 10 and 11. This is also noticeable in a comparison of the computer generated finite element analysis modeling of the two stent designs in FIGS. 12 and 16. As a result, the new stent design of FIGS. 13, 14, and 15, has reduced the strain exhibited about opening end 47 to less then four percent with the resulting elimination of noticeable fractures, cracks, or gaps in this area of the stent. This was confirmed during the manufacture process of this particularly sized stent as described herein. Thus the manufacturing yield of the stent is increased significantly to that of 85 to 90 percent. Comparison of the strain contours of the tensile strain or stretch in the ends of first and third T-shaped struts 39 and 41 indicate a further distribution of the strain about the strut ends and the elimination in FIG. 16 of any strain above four percent. This represents a significant advantage in the manufacture of the stents during the radial expansion to the expanded, larger diameter condition of the hoop cell. In addition, the finite element analysis revealed no significant strain increase in the C-shaped bend strut interconnections so as to cause fractures, cracks, or gaps during radial expansion.

Figure 17:
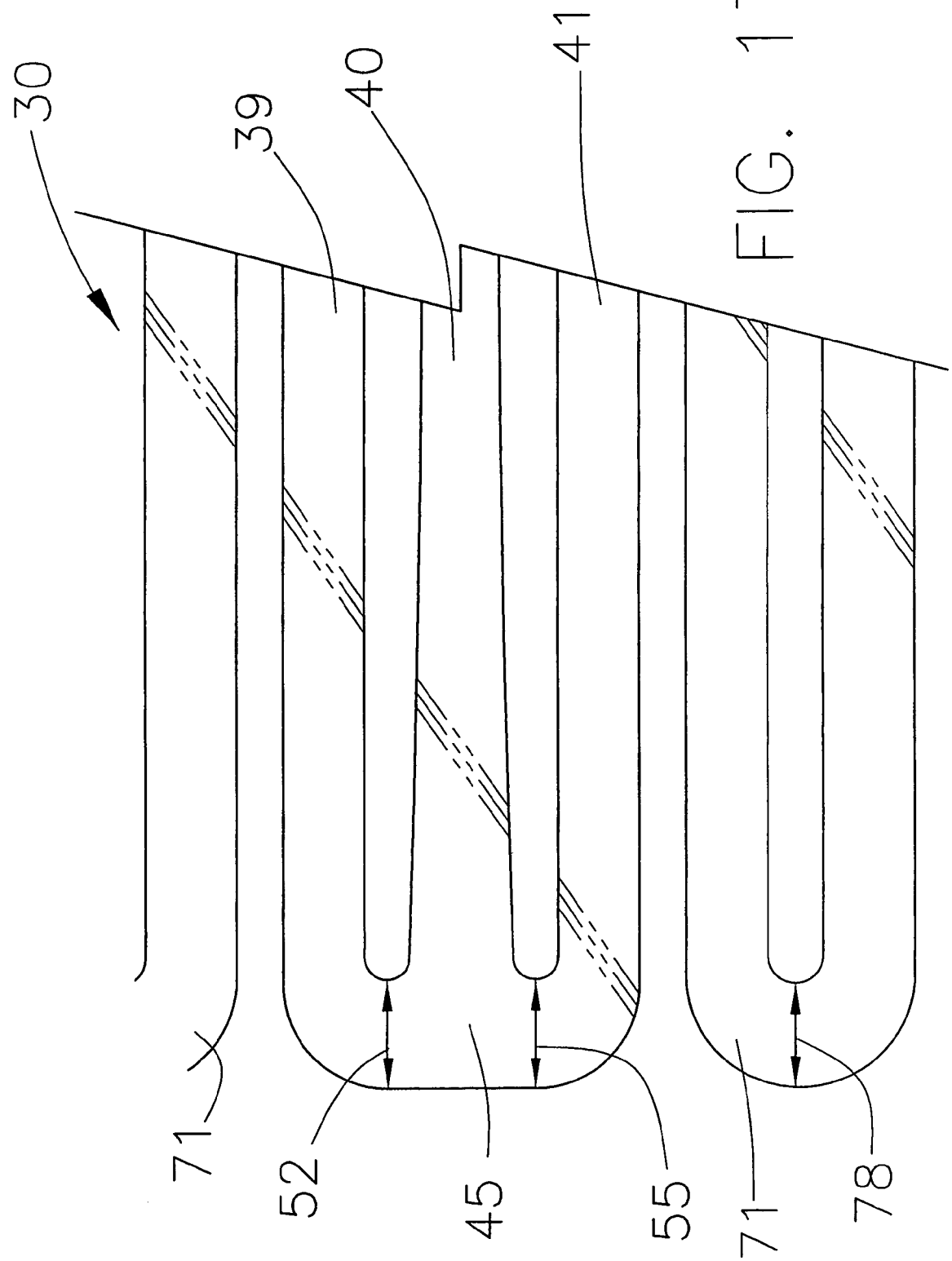
FIG. 17 depicts an enlarged flat view of yet another illustrative embodiment of the T-shaped and C-shaped strut interconnections in the hoop cell segment of the stent of the present invention with an increase in tip length of the struts at the T-shaped and C-shaped strut interconnections.

FIG. 17 depicts an enlarged flat view of yet another illustrative embodiment of stent 30 of the present invention and of FIG. 10 with an increase in tip lengths 52 and 55 of first and third struts 39 and 41 in the T-shaped strut interconnection. The geometry of the T-shaped and C-shaped strut interconnections 45 and 71 are the same as that of stent FIG. 10 except that first and second strut tip lengths 52 and 55 along with tip length 78 have been increased from the previous 0.18 mm length to for example 0.2 mm as suggested in the stent design of FIGS. 13, 14, and 15. This enlarged view of T-shaped strut interconnection 45 as well as C-shaped interconnections, curves or bights 71 has been provided to compare an increase in just the tip lengths of the struts to that of the performance of the stent of FIGS. 10 and 11.

Figure 18:
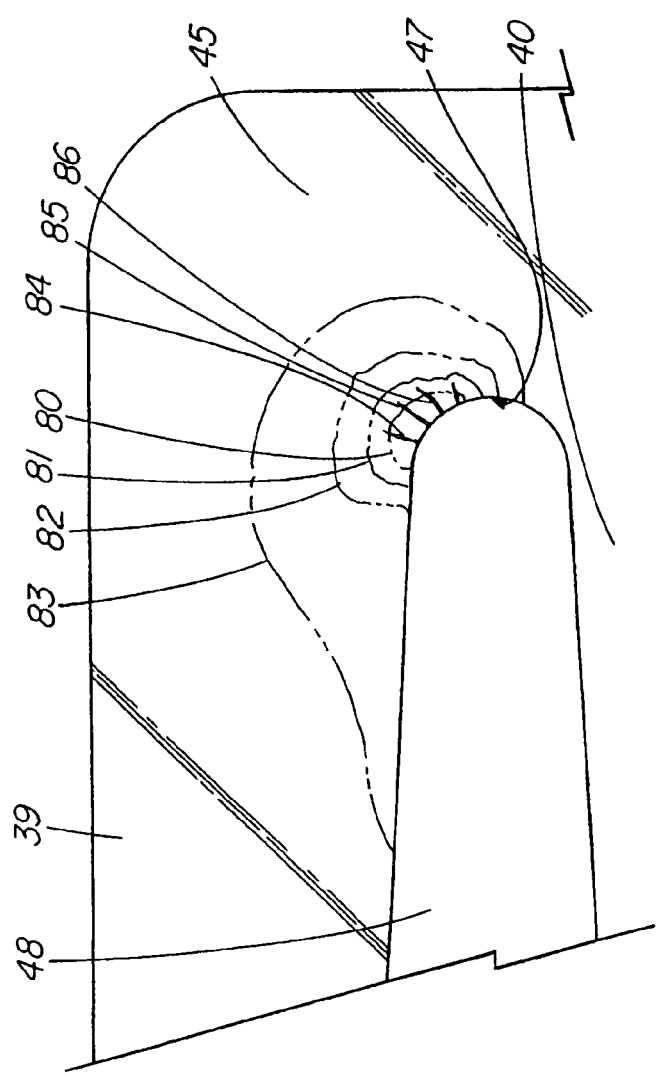
FIG. 18 depicts an enlarged flat view of a portion of the T-shaped strut interconnection of the stent of FIG. 17 exhibiting tensile strain or stretch therein after radial expansion.

FIG. 18 depicts an enlarged flat view of a portion of a T-shaped strut interconnection 45 of the stent of FIG. 17 with first strut 39 and second strut 40 exhibiting tensile strain or stretch after radial expansion. After radial expansion, the strain is exhibited at the strut end about first opening end 47 as depicted by strain contour lines 80, 81, 82 and 83. Outside of maximum strain contour line 83, the strain is less then one percent. Between strain contour lines 82 and 83, the strain varies between one and two percent. Between contour lines 81 and 82, the strain varies between two and three percent. Between strain contour lines, 80 and 81 the strain varies between three and four percent. The strain between strain contour line 80 and first opening end 47 is between four and 6.814 percent. As with the strain diagram of FIG. 12, there is a high concentration of tensile strain or stretch about first opening end 47 and contour line 80, the result is often that fractures, cracks, or gaps such as fractures, cracks, or gaps 84, 85, and 86 occur in this area and extend into the other areas of the struts such as between strain contour lines 80 and 81. These fractures, cracks, or gaps result from the radial expansion of the hoop cell to an enlarged diameter for heat set treatment. The increase in the tip length has produced strain contour lines very similar to that of FIG. 12 except that the strain between contour lines 82 and 83 has been extended a bit more over the length of first strut 39. However, the increase in the tip length has resulted in an even higher concentration of strain or stretch between opening end 47 and contour line 80. The maximum tensile strain or stretch in this area between the opening end and contour line 80 is now 6.814 percent compared to 5.662 percent of the stent of FIG. 12. This represents a nearly 1.2 percent difference in strain thus providing for a higher likelihood of fractures, cracks, or gaps in this area. Furthermore, this represents an increase of approximately 1.86 percent difference over that of the new stent design depicted in FIGS. 13, 14, and 15. This further supports that increasing the selected width of the longitudinal strut end about the opening end is the most significant factor in reducing strain in the strut end about the opening end to a level that will not cause fractures, cracks, or gaps in the high tensile strain area. The increase in tip length of the stent of FIG. 17 has spread out the distribution of strain, but increased the percent of tensile strain in a concentrated area to again facilitate the creation of fractures, cracks, or gaps during radial expansion of the hoop cell. However, increasing the tip length due to an increase in selected strut width helps distribute the stress and strain during pulsatile movement of the stent.

Figure 20:
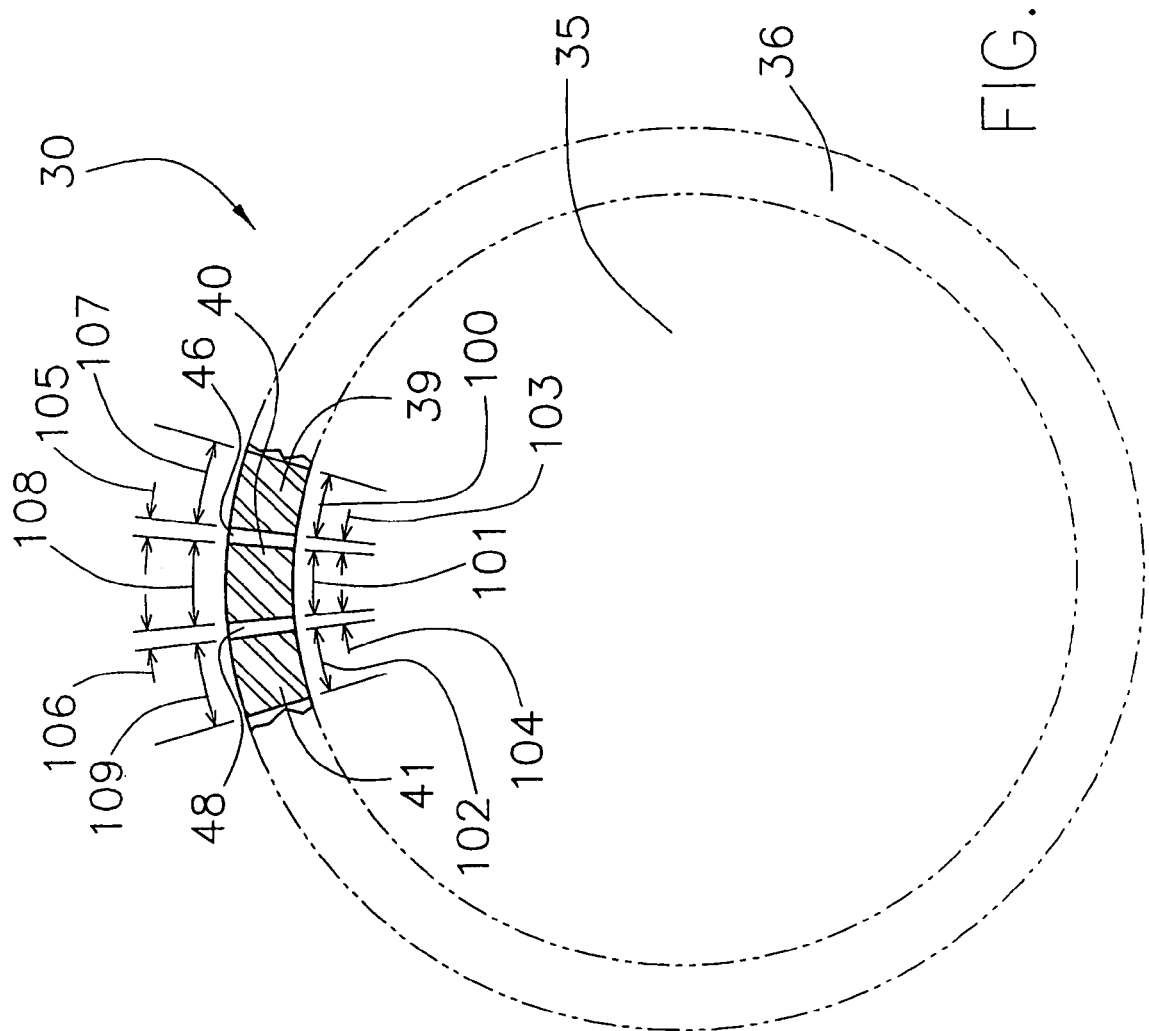
FIG. 20 depicts an enlarged cross-sectional end view of the stent of FIGS. 13 and 14 along the line 20, 21.

FIG. 20 depicts an enlarged cross-sectional end view of stent 30 of FIGS. 13 and 14 taken along the line 20, 21. This cross-sectional end view of stent 30 is through the minor axis of the at least partially first and third elliptical shapes 89 and 90 of first and second openings 46 and 48. This cross-sectional end view illustrates that first, second and third struts 39, 40 and 41 have different selected widths along the outside diameter of the cannula tube than that of the selected widths along the inside diameter of the cannula tube. Likewise, since first and second elongated openings 46 and 48 are cut in the cannula tube using for example a laser beam, the width of the elongated opening at the outside diameter of the cannula tube is greater than the width of the elongated opening along the inside diameter of the cannula tube. In particular, first longitudinal strut 39 has an outside diameter selected strut width 107 of for example 0.151 mm and an inside diameter selected strut width 100 of for example 0.109 mm. The difference between the outside and inside diameter selected strut width is of course due to the laser beam cutting through the cannula tube while being directed at the axis of the tube. Likewise, third strut 41 has outside diameter selected strut width 109 of for example 0.151 mm and inside diameter selected strut width 102 of for example 0.109 mm. Second longitudinal strut 40 has an outside diameter selected strut width 108 of for example 0.176 mm and inside diameter selected strut width 101 of for example 0.135 mm. Again, the greater outside diameter selected strut width is greater than the inside diameter selected strut width due to the cylindrical laser beam cutting the cannula tube. As a result, the selected width of the struts is less along the inside diameter of the cannula tube than that along the outside diameter of the cannula tube. This difference in selected width makes the selected width of the strut along the inside diameter of the cannula tube more susceptible to fracturing, cracking, or opening when the cannula tube is expanded to a larger diameter in manufacturing of the stent.

Figure 21:
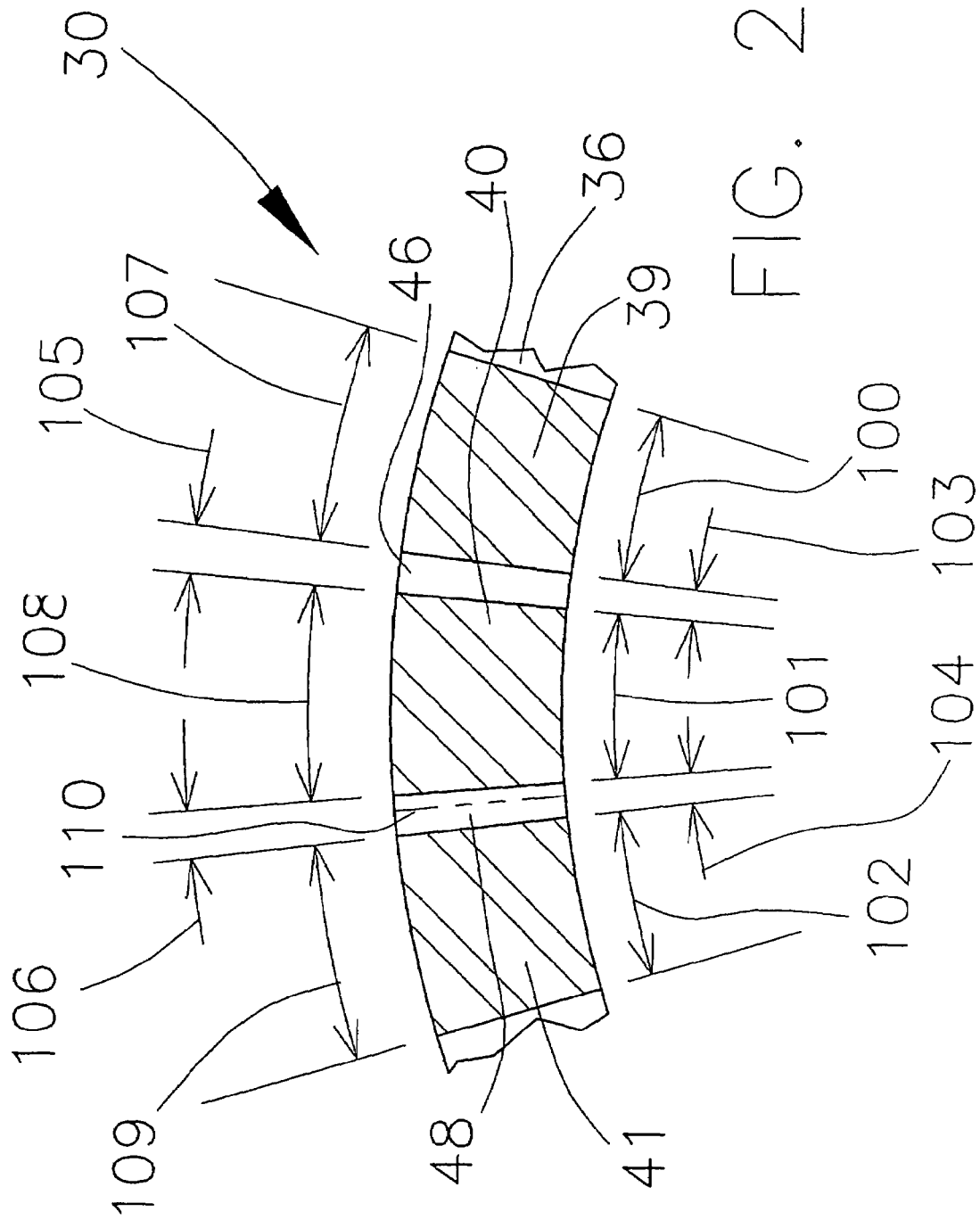
FIG. 21 depicts an enlarged portion of the cross-sectional end view of the stent of FIG. 20 through the minor axis of the elliptically shaped elongated openings.

FIG. 21 depicts an enlarged portion of the cross-sectional end view of stent 30 of FIG. 20. First longitudinal strut 39 has outside diameter selected strut width 107 and inside diameter selected strut width 100. As previously indicated, a first strut width ratio of the inside diameter strut width to the outside strut width is thus established. Utilizing the sample dimensions of 0.109 mm for the inside diameter strut width and 0.151 mm for the outside diameter strut width, first selected strut width ratio is thus 0.72185. Along uniform selected width 50 of the first strut, the outside diameter selected width is 0.140 mm and the inside diameter selected width is 0.098 mm. Thus, the first selected strut width ratio along the uniform width portion of the strut is 0.700. Comparing these two ratios of 0.700 and 0.72185, indicates that there is an increase of the inside diameter selected width to that of the outside diameter selected width of approximately three percent. This additional inside diameter width helps distribute the tensile strain experienced during radial expansion of the stent in manufacture. Although it may appear to be a small increase in width, this increase can readily be the difference between fractures, cracks or gaps appearing about the opening ends at the strut interconnections. The same figures are available for that of third longitudinal strut 41 when comparing outside diameter selected width 109 of that of inside diameter selected width 102.

Another comparison of the outside diameter to the inside diameter selected width is that of second longitudinal strut 40. In this particular embodiment of the stent, the width of the second strut decreases toward the strut interconnection. Along uniform selected width 74 of second strut 40, the outside diameter selected width is approximately 0.223 mm and the inside diameter selected width is 0.18 mm. The ratio of the outside diameter to the inside diameter selected width is thus 0.81166. The outside diameter selected width 108 of second strut 40 through the minor axis of the elliptically shaped longitudinal openings is 0.176 mm. The inside diameter selected width through the same cross-sectional area is 0.135 mm. Accordingly, the ratio of the inside and outside selected strut widths is 0.767. Thus the ratio of the inside to outside diameter selected width decreases through the elliptical shaped openings of the stent. Since the second strut experiences very little if any critical tensile strain, the decrease in this ratio has no appreciable adverse affect.

Attention is now directed to the outside and inside diameter widths of first and second openings 46 and 48. During manufacture, the laser beam creates a single pass opening of approximately 0.026 mm through the inside and outside diameters 103, 105 and 104, 106. Since the inside and outside diameter widths are the same, the ratio of the two is one. Through the elliptically shaped portion of the opening about the end of first and second elongated openings 46 and 48, the laser beam remains in place while the cannula tube is rotated to facilitate the at least elliptically shaped openings 89 and 90. As a result, outside diameter selected width 105 of first opening 46 is approximately 0.040 mm, whereas inside diameter selected width 103 of opening 46 is approximately 0.037 mm. Thus, the ratio of the inside to the outside diameter widths of the openings through the minor axis of the at least partially elliptically shaped opening is now less than one and in particular 0.925. The decrease in this ratio allows for the increase of the first selected strut width ratio. This is likewise the same case for inside and outside diameter widths 104 and 106 of second opening 48. Dotted line 110 represents the uniform cylindrical width of the laser beam during cutting of the cannula tube.

Figure 22:
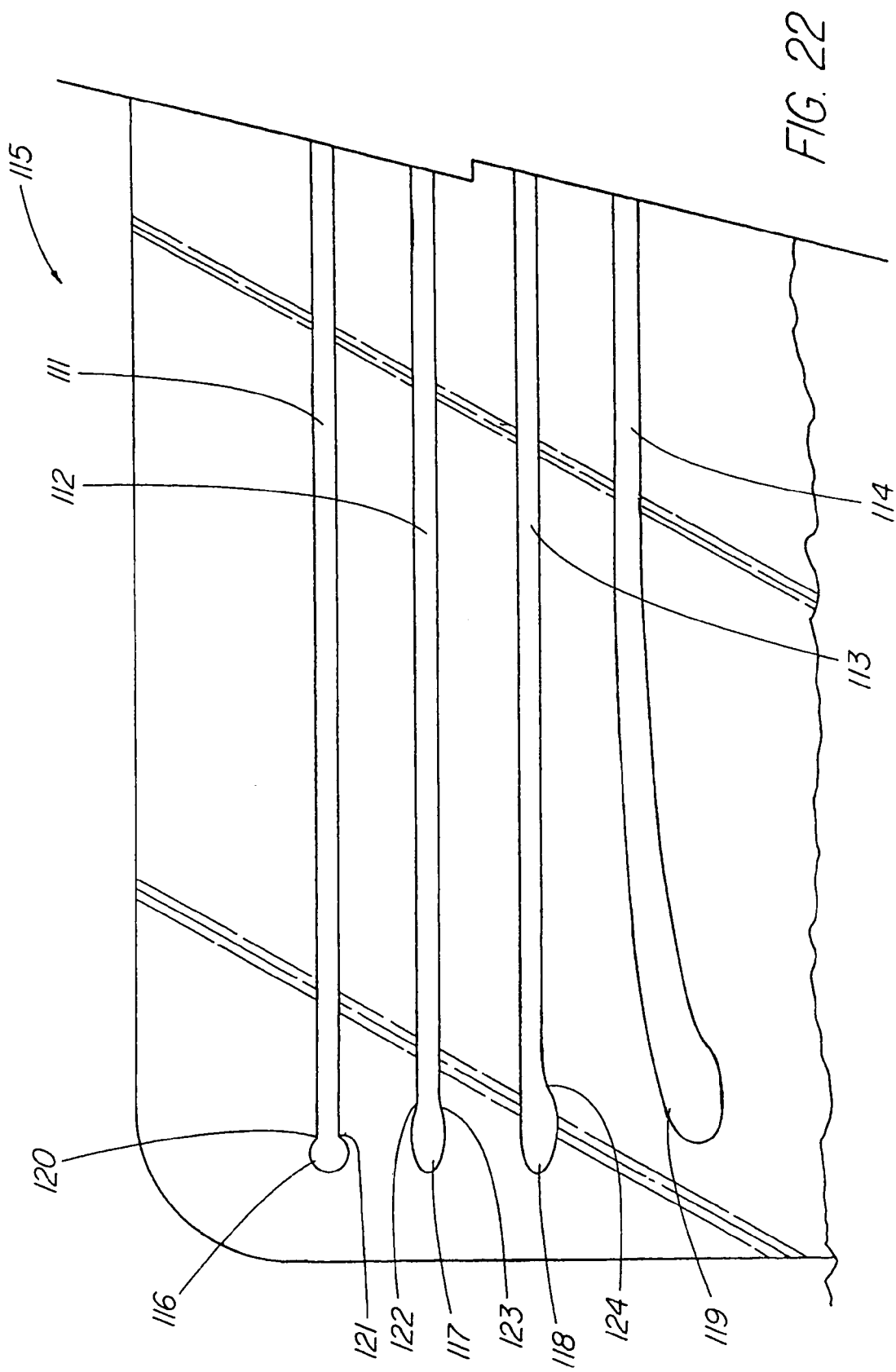
FIG. 22 depicts a plurality of elongated openings having differently shaped opening ends to help illustrate how the concentration of tensile strain can be minimized.

FIG. 22 depicts a plurality of different elongated openings 111 through 114 cut in stent 115 of the present invention. At one end of opening 111 is a circular shaped opening 116 which creates two sharp edges 120 and 121. These sharp edges at the end of an elongated opening are susceptible to fractures, cracks, or gaps appearing thereat during radial expansion in manufacture of a stent. This, of course, is due to the tensile strain being concentrated at these points. Thus simply increasing the width of the elongated opening or slot does not eliminate the problems of tensile strain being concentrated thereat particularly in a circular configuration. Elliptically shaped opening 117 at the end of elongated 112 also creates two sharp edges 122 and 123. These sharp edges are not as pointed as edges 120 and 121, but are susceptible to concentrating tensile strain thereat during radial expansion of the stent. Elliptically shaped opening 118 at the end of elongated opening or slot 113 has been tangentially blended into elongated opening 113. Thus, an undesirable edge has been eliminated from the strut for the purposes of concentrating tensile strain thereat. Edge 124 has been radiused, but is along the tie bar of a T-shaped interconnection and thus does not experience any high concentrations of tensile strain when the stent is radially expanded in manufacture. Elliptically shaped opening 119 at the end of elongated opening or slot 114 best exemplifies the principles of the present invention in that elliptically shaped opening 119 is tangentially blended into elongated opening 114, thereby eliminating any edge for the concentration of tensile strain during radial expansion. Furthermore, the elongated opening 114 has been radiused toward elliptically shaped opening 118 for the purposes of increasing the width of a side strut in a T-shaped strut interconnection.

It is to be understood that the above-described stent are merely illustrative embodiments of the principles of this invention and that other stents may be devised by those skilled in the art without departing from the spirit and scope of this invention. In particular, the various longitudinal struts of the herein described stents have been characterized as being typically longitudinal and having for the most part a uniform width. However, the width may be varied along the length of any strut at either strut end or anywhere in between for the purposes of more evenly distributing tensile strain along the length of the strut and away from critical areas such as strut ends which are subject to high tensile strain during radial and pulsatile expansion and contraction. Simply changing the width of one strut end may help distribute the strain from that end; however, since the hoop flex cell segments are circumferential, lessening strain at one end of a strut may disadvantageously increase the strain at another end of the same or another interconnected strut. The ends of the longitudinal struts have been selectively increased at a T-shaped interconnection to minimize excessive strain and resulting fractures, cracks, or gaps thereat. The tip length at these T-shaped interconnections has also been varied and in particular lengthened in combination with selectively increasing the width of the strut end. These two dimensions can be altered in combination along with rounding or changing the radii of the elongated opening end to again reduce strain experienced during radial expansion. The opposite end of these T-shaped interconnection struts have also had their tip length increased to help distribute the strain along the length of the strut. The T-shaped interconnection presents a unique situation in which a longitudinal strut or tie bar does not appreciably affect or receive tensile strain therein. Accordingly, the combination of adjusting adjacent strut tip length width and radii are understood to be varied to produce an acceptable strain at any point around the radially expandable segment.

What is claimed is:

1. A cannula stent comprising:
a cannula having a passageway extending longitudinally therein and a wall of biocompatible material extending at least partially around said passageway, said wall having a plurality of struts extending longitudinally therein and a plurality of elongated openings therethrough, said openings extending at least partially between said plurality of struts, at least first, second, and third ones of said struts being adjacent and having respective ends laterally interconnected at a strut interconnection, a first opening of said openings extending between the first and the second struts and having a first opening end longitudinally adjacent the strut interconnection between the first and the second struts, a second opening of said openings extending between the second and the third struts and having a second opening end longitudinally adjacent the strut interconnection between the second and the third struts, wherein the first strut has a selected width that increases along the first strut toward the first opening end and wherein the second strut has a selected width that decreases along the second strut toward the strut interconnection.

2. The cannula stent of claim 1 wherein the third strut has a selected width that increases along the third strut toward the second opening end.

3. The cannula stent of claim 2 wherein the selected width of the third strut increases longitudinally along the third strut toward the second opening end.

4. The cannula stent of claim 2 wherein the third selected width of the third strut has a third outside diameter selected width and a third inside diameter selected width less than the third outside diameter selected width.

5. The cannula stent of claim 1 wherein the selected width of the first strut increases longitudinally along the first strut toward the first opening end.

6. The cannula stent of claim 1 wherein the strut interconnection has a first interconnection length that extends longitudinally from the first opening end to a first edge of the strut interconnection that is longitudinally opposite the first opening end, wherein the selected width of the first strut extends at least partially along a length of the first strut, and wherein the first interconnection length is greater than the selected width of the first strut.

7. The cannula stent of claim 6 wherein the first interconnection length is greater than the selected width of the first strut by 10 to 30 percent.

8. The cannula stent of claim 6 wherein the first interconnection length is greater than the selected width of the first strut by 15 to 25 percent.

9. The cannula sent of claim 6 wherein the first interconnection length is greater than the selected width of the first strut by about 20 percent.

10. The cannula stent of claim 6 wherein the strut interconnection has a second interconnection length that extends longitudinally from the second opening end to a second edge of the strut interconnection that is longitudinally opposite the second opening end, wherein the selected width of the third strut extends at least partially along a length of the third strut, and wherein the second interconnection length is greater than the selected width of the third strut.

11. The cannula stent of claim 10 wherein the second interconnection length is greater than the selected width of the third strut by 10 to 30 percent.

12. The cannula stent of claim 10 wherein the first and the second interconnection lengths are equivalent.

13. The cannula stent of claim 10 wherein the second interconnection length is greater than the selected width of the third strut by 15 to 25 percent.

14. The cannula stent of claim 10 wherein the second interconnection length is greater that the selected width of the third strut by about 20 percent.

15. The cannula stent of claim 2 wherein the first and the second opening ends are laterally adjacent.

16. The cannula stent of claim 2 wherein the selected widths of the first and the third struts are equivalent and wherein the increases of the selected widths of the first and the third struts are equivalent.

17. The cannula stent of claim 2 wherein the first and the second opening ends have the same axial position along the cannula.

18. The cannula stent of claim 2 wherein the increases of the selected widths of the first and the third struts are over an equivalent length of the first and the third struts.

19. The cannula stent of claim 18 wherein the increases of the selected widths of the first and the third struts are over 10 to 30 percent of the lengths of the first and the third struts.

20. The cannula stent of claim 18 wherein the increases of the selected widths are over 12.5 to 25 percent of the lengths of the first end the third struts.

21. The cannula stent of claim 18 wherein the increases of the selected widths of the first and the third struts are over less than 20 percent of the lengths of the first and the third struts.

22. The cannula stent of claim 2 wherein the width of the first and the second elongated openings is greater about the first and the second opening ends than the remainder of the first and the second elongated openings between the first and the second struts and between the second and the third struts, respectively.

23. The cannula stent of claim 2 wherein the first and the second elongated openings are rounded about the first and the second opening ends.

24. The cannula stent of claim 23 wherein the first and the second elongated openings are at least partially elliptical about the first and the second opening ends.

25. The cannula stent of claim 2 wherein the respective ends of the first and the third struts at the strut interconnection are rounded.

26. The cannula stent of claim 25 wherein the respective ends of the first and the third struts at the strut interconnection are convex.

27. The cannula stent of claim 26 wherein the respective end of the second strut at the strut interconnection is concave.

28. A cannula stent comprising:
a cannula having a passageway extending longitudinally therein end a wall of biocompatible material extending at least partially around said passageway, said wall having a plurality of struts extending longitudinally therein and a plurality of elongated openings therethrough, said openings extending at least partially between said plurality of struts, at least first, second, and third ones of said struts being adjacent and having respective ends laterally interconnected at a strut interconnection, a first opening of said openings extending between the first and the second struts and having a first opening end longitudinally adjacent the strut interconnection between the first and the second struts, a second opening of said openings extending between the second and the third struts and having a second opening end longitudinally adjacent the strut interconnection between the second and the third struts, wherein the first and the second openings are equivalent in shape and at least partially elliptical and the first and the second opening ends are positioned at the same axial position along the elongated member, wherein the first strut has a width that increases along the first strut toward the first opening end and wherein the second strut has a selected width that decreases along the second strut toward the strut interconnection.

29. The cannula stent of claim 1 wherein the first selected width of the first strut has a first outside diameter selected width and a first inside diameter selected width less than the first outside diameter selected width.

30. The cannula stent of claim 29 wherein the first inside diameter selected width to the first outside diameter selected width establishes a first selected strut width ratio.

31. The cannula stent of claim 30 wherein the first selected strut width ratio increases along the first strut toward the first opening end.

32. The cannula stent of claim 31 wherein the first elongated opening is at least partially elliptical about the first opening end and wherein the first selected strut width ratio increases more rapidly along the first elongated opening where at least partially elliptical than the remaining portion of the first elongated opening.

33. The cannule stent of claim 1 wherein the first elongated opening is at least partially elliptical about the first opening end; wherein the first elongated opening has a first outside diameter opening width and a first inside diameter opening width; wherein the first inside diameter opening width to the first outside diameter opening width establishes a first opening width ratio; and wherein the first opening width ratio decreases along the first elongated opening where at least partially elliptical.

* * * * *